(12) United States Patent
Elmore et al.

(10) Patent No.: US 7,030,115 B2
(45) Date of Patent: Apr. 18, 2006

(54) N-SULFONYLUREA APOPTOSIS PROMOTERS

(75) Inventors: Steven W. Elmore, Gurnee, IL (US); Cheol-Min Park, Gurnee, IL (US); Xilu Wang, Graylake, IL (US)

(73) Assignee: Abbott Laboratories, Abbott Park, IL (US)

( * ) Notice: Subject to any disclaimer, the term of this patent is extended or adjusted under 35 U.S.C. 154(b) by 259 days.

(21) Appl. No.: 10/394,985

(22) Filed: Mar. 21, 2003

(65) Prior Publication Data

US 2003/0236247 A1     Dec. 25, 2003

Related U.S. Application Data

(60) Provisional application No. 60/366,442, filed on Mar. 21, 2002.

(51) Int. Cl.
*A61K 31/5377* (2006.01)
*A61K 31/495* (2006.01)
*C07D 295/195* (2006.01)
*C07D 413/10* (2006.01)

(52) U.S. Cl. ............... 514/235.8; 514/255.01; 514/330; 514/354; 544/121; 544/390; 546/226; 546/324

(58) Field of Classification Search ........... 544/390, 544/121; 514/235.8, 255.01
See application file for complete search history.

(56) References Cited

U.S. PATENT DOCUMENTS

| 6,169,088 B1 * | 1/2001 | Matsuno et al. | 514/252.16 |
| 2002/0086887 A1 | 7/2002 | Augeri et al. | 514/354 |

FOREIGN PATENT DOCUMENTS

| EP | 0 882 717 | 12/1998 |
| WO | 01/47891 | 12/2000 |
| WO | 02/24636 | 3/2002 |
| WO | 2003/080586 | * 10/2003 |

OTHER PUBLICATIONS

Khorchid et al. Expert Opin. Ther. Patents vol. 14, p. 805-818 (2004).*

* cited by examiner

*Primary Examiner*—Emily Bernhardt
(74) *Attorney, Agent, or Firm*—B. Gregory Donner

(57) ABSTRACT

Compounds having the formula

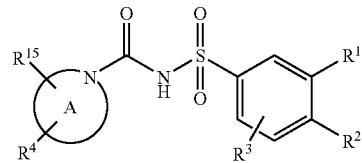

are apoptosis promoters. Also disclosed are methods of making the compounds, compositions containing the compounds, and methods of treatment using the compounds.

6 Claims, No Drawings

US 7,030,115 B2

N-SULFONYLUREA APOPTOSIS PROMOTERS

This application claims priority to U.S. Provisional Application Ser. No. 60/366,442, filed Mar. 21, 2002.

TECHNICAL FIELD

The present invention relates to substituted N-sulfonylureas which are useful for promoting apoptosis, methods of making the compounds, compositions containing the compounds, and methods of treatment using the compounds.

BACKGROUND OF THE INVENTION

Apoptosis is a mode of cell death in which the cell commits suicide either to ensure proper development of the organism or to destroy cells that represent a threat to the organism's integrity. Morphologically, apoptosis is characterized by blebbing of the plasma membrane, shrinking of the cytoplasm and nucleus, and fragmenting into particles which are engulfed by phagocytic cells. Although apoptosis plays a critical role in normal development, its impairment is thought to be a significant factor in the etiology of such diseases as cancer, autoimmune disorders, inflammatory diseases, and viral infections. Conversely, increased apoptosis has been linked to AIDS and neurodegenerative diseases such as Parkinson's disease, stroke, and Alzheimer's disease.

Bcl-$X_L$ is a protein which, in healthy cells, is expressed in the outer membranes of the mitochondria, the endoplasmic reticulum, and the nuclear envelope. Its function is to bind to specific protein/protease complexes and prevent cell apoptosis. Upon internal damage to the cell the protein/protease complexes are released, and cause the process of apoptosis to begin. An over-expression of Bcl-$X_L$, often present in cancerous and other diseased cells, results in the blocking of apoptotic signals and allows the cells to proliferate. It is believed that by blocking BCl-$X_L$, apoptosis can be induced in diseased cells, and can provide an effective therapy for cancer and other diseases caused by the impairment of the apoptotic process. Based on these findings and the absence of small molecule BCl-$X_L$ inhibitors from current cancer therapies, there is a continuing need for compounds which can trigger apoptosis through the inhibition of the Bcl family of proteins.

SUMMARY OF THE INVENTION

In its principle embodiment, the present invention provides a compound of formula (I)

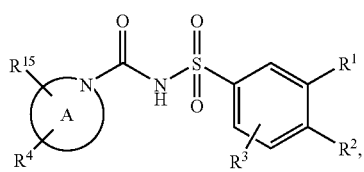

(I)

or a therapeutically acceptable salt thereof, wherein

A is a five-, six-, or seven-membered non-aromatic ring containing a nitrogen atom wherein from zero to two carbon atoms are replaced by a heteroatom selected from the group consisting of nitrogen, oxygen, and sulfur;

$R^1$ is selected from the group consisting of alkyl, cyano, halo, haloalkyl, nitro, and —$NR^5R^6$;

$R^2$, and $R^3$ are independently selected from the group consisting of hydrogen, alkenyl, alkoxy, alkyl, alkylcarbonyloxy, alkylsulfanyl, alkynyl, aryl, arylalkoxy, aryloxy, aryloxyalkoxy, arylsulfanyl, arylsulfanylalkoxy, cycloalkylalkoxy, cycloalkyloxy, halo, haloalkoxy, haloalkyl, heterocycle, (heterocycle)oxy, hydroxy, nitro, and —$NR^5R^6$;

$R^4$ is selected from the group consisting of aryl, arylalkenyl, arylalkoxy, cycloalkenyl, cycloalkyl, halo, heterocycle, and (heterocycle)alkoxy;

$R^5$ and $R^6$ are independently selected from the group consisting of hydrogen, alkenyl, alkoxyalkyl, alkoxycarbonylalkyl, alkyl, alkylsulfanylalkyl, alkylsulfonylalkyl, aryl, arylalkyl, arylalkylsulfanylalkyl, aryloxyalkyl, arylsulfanylalkyl, arylsulfinylalkyl, arylsulfonylalkyl, carboxyalkyl, cycloalkenyl, cycloalkenylalkyl, cycloalkyl, (cycloalkyl)alkyl, cycloalkylcarbonyl, heterocycle, (heterocycle)alkyl, (heterocycle)sulfanylalkyl, hydroxyalkyl, and a nitrogen protecting group; or $R^5$ and $R^6$, together with the nitrogen atom to which they are attached, form a ring selected from the group consisting of imidazolyl, morpholinyl, piperazinyl, piperidinyl, pyrrolidinyl, pyrrolyl, thiomorpholinyl, and thiomorpholinyl dioxide; and $R^{15}$ is selected from the group consisting of hydrogen, alkoxy, alkyl, and halo.

In another embodiment, the present invention discloses a pharmaceutical composition comprising a compound of formula (I), or a therapeutically acceptable salt thereof, in combination with a therapeutically acceptable carrier.

In another embodiment, the present invention discloses a method of promoting apoptosis in a mammal in recognized need of such treatment comprising administering to the mammal a therapeutically acceptable amount of a compound of formula (I), or a therapeutically acceptable salt thereof.

DETAILED DESCRIPTION OF THE INVENTION

Compounds of the present invention comprise substituted arylsulfonamides which are useful for the treatment of apoptosis-mediated diseases.

As used in the present specification the following terms have the meanings indicated:

The term "alkenyl," as used herein, represents a straight or branched chain group of one to twelve carbon atoms derived from a straight or branched chain hydrocarbon containing at least one carbon-carbon double bond.

The term "alkenylene," as used herein, represents a group of two to six atoms derived from an unsaturated straight or branched chain hydrocarbon.

The term "alkoxy," as used herein, represents an alkyl group attached to the parent molecular moiety through an oxygen atom.

The term "alkoxyalkoxy," as used herein, represents an alkoxy group attached to the parent molecular moiety through another alkoxy group.

The term "alkoxyalkoxyalkyl," as used herein, represents an alkoxyalkoxy group attached to the parent molecular moiety through an alkyl group.

The term "alkoxyalkoxycarbonyl," as used herein, represents an alkoxyalkoxy group attached to the parent molecular moiety through a carbonyl group.

The term "alkoxyalkyl," as used herein, represents an alkoxy group attached to the parent molecular moiety through an alkyl group.

The term "alkoxyalkylcarbonyl," as used herein, represents an alkoxyalkyl group attached to the parent molecular moiety through a carbonyl group.

The term "alkoxycarbonyl," as used herein, represents an alkoxy group attached to the parent molecular moiety through a carbonyl group.

The term "alkoxycarbonylalkyl," as used herein, represents an alkoxycarbonyl group attached to the parent molecular moiety through an alkyl group.

The term "alkyl," as used herein, represents a group of one to twelve carbon atoms derived from a straight or branched chain saturated hydrocarbon.

The term "alkylamino," as used herein, represents —N($R^{14}$)$_2$, wherein $R^{14}$ is alkyl.

The term "alkylaminoalkyl," as used herein, represents an alkylamino group attached to the parent molecular moiety through an alkyl group.

The term "alkylaminocarbonyl," as used herein, represents an alkylamino group attached to the parent molecular moiety through a carbonyl group.

The term "alkylaminocarbonylalkyl," as used herein, represents an alkylaminocarbonyl group attached to the parent molecular moiety through an alkyl group.

The term "alkylcarbonyl," as used herein, represents an alkyl group attached to the parent molecular moiety through a carbonyl group. The alkylcarbonyl groups of this invention can be optionally substituted with one or two groups independently selected from the group consisting of hydroxy and —N$R^5R^6$, wherein $R^5$ and $R^6$ are as previously defined.

The term "alkylcarbonylalkyl," as used herein, represents an alkylcarbonyl group attached to the parent molecular moiety through an alkyl group.

The term "alkylcarbonyloxy," as used herein, represents an alkylcarbonyl group attached to the parent molecular moiety through an oxygen atom.

The term "alkylene," as used herein, represents a group of two to six atoms derived from a saturated straight or branched chain hydrocarbon.

The term "alkylidene," as used herein, refers to an alkenyl group in which one carbon atom of the carbon-carbon double bond belongs to the moiety to which the alkenyl group is attached.

The term "alkylsulfanyl," as used herein, represents an alkyl group attached to the parent molecular moiety through a sulfur atom.

The term "alkylsulfanylalkyl," as used herein, represents an alkylsulfanyl group attached to the parent molecular moiety through an alkyl group.

The term "alkylsulfonyl," as used herein, represents an alkyl group attached to the parent molecular moiety through a sulfonyl group.

The term "alkylsulfonylalkyl," as used herein, represents an alkylsulfonyl group attached to the parent molecular moiety through an alkyl group.

The term "alkynyl," as used herein, represents a straight or branched chain group of one to twelve carbon atoms containing at least one carbon-carbon triple bond.

The term "amino," as used herein, represents —N$R^9R^{10}$, wherein $R^9$ and $R^{10}$ are independently selected from the group consisting of hydrogen, alkenyl, alkoxyalkyl, alkoxyalkoxyalkyl, alkoxycarbonyl, alkyl, alkylaminoalkyl, alkylaminocarbonylalkyl, alkylcarbonyl, aryl, arylalkoxycarbonyl, arylalkyl, arylalkylcarbonyl, arylcarbonyl, arylsulfonyl, cycloalkyl, (cycloalkyl)alkyl, cycloalkylcarbonyl, haloalkyl, haloalkylcarbonyl, heterocycle, (heterocycle)alkyl, heterocyclecarbonyl, hydroxyalkyl, a nitrogen protecting group, —C(NH)NH$_2$, and —C(O)(CH$_2$)$_n$N$R^5R^6$, wherein n is 0, 1, 2, or 3; and $R^5$ and $R^6$ are as previously defined; wherein the aryl; the aryl part of the arylalkoxycarbonyl, the arylalkyl, the arylalkylcarbonyl, the arylcarbonyl, and the arylsulfonyl; the cycloalkyl; the cycloalkyl part of the (cycloalkyl)alkyl and the cycloalkylcarbonyl; the heterocycle; and the heterocycle part of the (heterocycle)alkyl and the heterocyclecarbonyl can be optionally substituted with one, two, three, four, or five substituents independently selected from the group consisting of alkoxy, alkyl, alkylcarbonyl, cyano, halo, haloalkoxy, haloalkyl, hydroxy, and nitro.

The term "aminoalkoxy," as used herein, represents an amino group attached to the parent molecular moiety through an alkoxy group.

The term "aminoalkyl," as used herein, represents an amino group attached to the parent molecular moiety through an alkyl group.

The term "aminoalkylcarbonyl," as used herein, represents an amino group attached to the parent molecular moiety through an alkylcarbonyl group.

The term "aminocarbonyl," as used herein, represents an amino group attached to the parent molecular moiety through a carbonyl group.

The term "aminocarbonylalkyl," as used herein, represents an aminocarbonyl group attached to the parent molecular moiety through an alkyl group.

The term "aminosulfonyl," as used herein, represents an amino group attached to the parent molecular moiety through a sulfonyl group.

The term "aryl," as used herein, represents a phenyl group or a bicyclic or tricyclic fused ring system wherein one or more of the fused rings is a phenyl group. Bicyclic fused ring systems are exemplified by a phenyl group fused to a monocyclic cycloalkyl group as defined herein, a monocyclic cycloalkenyl group as defined herein, or another phenyl group. Tricyclic fused ring systems are exemplified by a bicyclic fused ring system fused to a monocyclic cycloalkyl group as defined herein, a monocyclic cycloalkenyl group as defined herein, or another phenyl group. Representative examples of aryl include, but are not limited to, anthracenyl, azulenyl, fluorenyl, indanyl, indenyl, naphthyl, phenyl, and tetrahydronaphthyl. Aryl groups having an unsaturated or partially saturated ring fused to an aromatic ring can be attached through the saturated or the unsaturated part of the group. The aryl groups of this invention can be optionally substituted with one, two, three, four, or five substituents independently selected from the group consisting of alkenyl, alkoxy, alkoxyalkyl, alkoxyalkylcarbonyl, alkoxycarbonyl, alkoxycarbonylalkyl, alkyl, alkylcarbonyl, alkylcarbonyloxy, alkynyl, amino, aminoalkyl, aminocarbonyl, aminocarbonylalkyl, aminosulfonyl, a second aryl group, arylalkoxy, aryloxy, arylsulfanyl, cyano, halo, haloalkoxy, haloalkyl, heterocycle, (heterocycle)alkyl, heterocyclecarbonylalkenyl, heterocyclecarbonylalkyl, hydroxy, hydroxyalkyl, nitro, oxo, and —C(NH)NH$_2$, wherein the second aryl group; the aryl part of the arylalkoxy, the aryloxy, and the arylsulfanyl; the heterocycle; and the heterocycle part of the (heterocycle)alkyl, the heterocyclecarbonylalkenyl, and the heterocyclecarbonylalkyl can be further optionally substituted with one, two, or three substituents independently selected from the group consisting of alkoxyalkylcarbonyl, alkoxycarbonyl, alkyl, alkylsulfonyl, aminocarbonyl, aminosulfonyl, cyano, halo, haloalkoxy, haloalkyl, hydroxy, nitro, oxo, and —C(NH)NH$_2$. In addition, the heterocycle and the heterocycle part of the (heterocycle)alkyl, the heterocyclecarbonylalkenyl, and the heterocyclecarbonylalkyl can be further optionally substituted with an additional aryl group, wherein the additional aryl group can be optionally substituted with one, two, or three substituents independently selected from the group consisting of alkoxy, alkyl, cyano, halo, hydroxy, and nitro.

The term "arylalkenyl," as used herein, represents an alkenyl group substituted by one, two, or three aryl groups.

The term "arylalkoxy," as used herein, represents an aryl group attached to the parent molecular moiety through an alkoxy group.

The term "arylalkoxyalkyl," as used herein, represents an arylalkoxy group attached to the parent molecular moiety through an alkyl group.

The term "arylalkoxyalkylcarbonyl," as used herein, represents an arylalkoxyalkyl group attached to the parent molecular moiety through a carbonyl group.

The term "arylalkoxycarbonyl," as used herein, represents an arylalkoxy group attached to the parent molecular moiety through a carbonyl group.

The term "arylalkyl," as used herein, represents an alkyl group substituted with one, two, or three aryl groups. The alkyl part of the arylalkyl can be optionally substituted with one or two amino groups.

The term "arylalkylcarbonyl," as used herein, represents an arylalkyl group attached to the parent molecular moiety through a carbonyl group.

The term "arylalkylidene," as used herein, represents an aryl group attached to the parent molecular moiety through an alkylidene group.

The term "arylalkylsulfanyl," as used herein, represents an arylalkyl group attached to the parent molecular moiety through a sulfur atom.

The term "arylalkylsulfanylalkyl," as used herein, represents an arylalkylsulfanyl group attached to the parent molecular moiety through an alkyl group.

The term "arylalkylsulfonyl," as used herein, represents an arylalkyl group attached to the parent molecular moiety through a sulfonyl group.

The term "arylcarbonyl," as used herein, represents an aryl group attached to the parent molecular moiety through a carbonyl group.

The term "aryloxy," as used herein, represents an aryl group attached to the parent molecular moiety through an oxygen atom.

The term "aryloxyalkoxy," as used herein, represents an aryloxy group attached to the parent molecular moiety through an alkoxy group.

The term "aryloxyalkyl," as used herein, represents an aryloxy group attached to the parent molecular moiety through an alkyl group.

The term "aryloxyalkylcarbonyl," as used herein, represents an aryloxyalkyl group attached to the parent molecular moiety through a carbonyl group.

The term "arylsulfanyl," as used herein, represents an aryl group attached to the parent molecular moiety through a sulfur atom.

The term "arylsulfanylalkoxy," as used herein, represents an arylsulfanyl group attached to the parent molecular moiety through an alkoxy group. The alkoxy part of the arylsulfanylalkoxy can be optionally substituted with one or two amino groups.

The term "arylsulfanylalkyl," as used herein, represents an arylsulfanyl group attached to the parent molecular moiety through an alkyl group. The alkyl part of the arylsulfanylalkyl can be optionally substituted with one or two substituents independently selected from the group consisting of alkoxy, alkoxycarbonyl, amino, aminoalkoxy, aminocarbonyl, arylalkoxy, azido, carboxy, cycloalkyl, halo, heterocycle, (heterocycle)alkoxy, (heterocycle)carbonyl, and hydroxy.

The term "arylsulfinyl," as used herein, represents an aryl group attached to the parent molecular moiety through a sulfinyl group.

The term "arylsulfinylalkyl," as used herein, represents an arylsulfinyl group attached to the parent molecular moiety through an alkyl group. The alkyl part of the arylsulfinylalkyl can be optionally substituted with one or two amino groups.

The term "arylsulfonyl," as used herein, represents an aryl group attached to the parent molecular moiety through a sulfonyl group.

The term "arylsulfonylalkyl," as used herein, represents an arylsulfonyl group attached to the parent molecular moiety through an alkyl group. The alkyl part of the arylsulfonylalkyl can be optionally substituted with one or two amino groups.

The term "azido," as used herein, represents —$N_3$.

The term "carbonyl," as used herein, represents —C(O)—.

The term "carboxy," as used herein, represents —$CO_2H$.

The term "carboxyalkyl," as used herein, represents a carboxy group attached to the parent molecular moiety through an alkyl group.

The term "cyano," as used herein, represents —CN.

The term "cyanoalkyl," as used herein, represents a cyano group attached to the parent molecular moiety through an alkyl group.

The term "cycloalkenyl," as used herein, represents a non-aromatic ring system having three to ten carbon atoms and one to three rings, wherein at least one ring is a five-membered ring with one double bond, a six-membered ring with one or two double bonds, a seven- or eight-membered ring with one to three double bonds, or a nine-to ten-membered ring with one to four double bonds. Examples of cycloalkenyl groups include cyclohexenyl, octahydronaphthalenyl, norbornylenyl, and the like. The cycloalkenyl groups of this invention can be optionally substituted with one, two, three, four, or five substituents independently selected from the group consisting of alkoxy, alkoxycarbonyl, alkyl, aminoalkyl, arylalkoxy, aryloxy, arylsulfanyl, halo, haloalkoxy, haloalkyl, and hydroxy, wherein the aryl part of the arylalkoxy, the aryloxy, and the arylsulfanyl can be further optionally substituted with one, two, or three substituents independently selected from the group consisting of alkoxy, alkyl, halo, haloalkoxy, haloalkyl, and hydroxy.

The term "cycloalkenylalkyl," as used herein, represents a cycloalkenyl group attached to the parent molecular moiety through an alkyl group.

The term "cycloalkyl," as used herein, represents a saturated ring system having three to twelve carbon atoms and one to three rings. Examples of cycloalkyl groups include cyclopropyl, cyclopentyl, bicyclo(3.1.1)heptyl, adamantyl, and the like. The cycloalkyl groups of this invention can be optionally substituted with one, two, three, four, or five substituents independently selected from the group consisting of alkoxy, alkoxycarbonyl, alkyl, alkylidene, amino, aminoalkoxy, aminoalkyl, aryl, arylalkenyl, arylalkoxy, arylalkyl, arylalkylidene, aryloxy, arylsulfanyl, a second cycloalkyl group, (cycloalkyl)alkyl, cycloalkylalkylidene, halo, haloalkoxy, haloalkyl, heterocycle, (heterocycle)alkoxy, (heterocycle)alkyl, (heterocycle)alkylidene, hydroxy, spirocycle, and spiroheterocycle; wherein the aryl; the aryl part of the arylalkenyl, the arylalkoxy, the arylalkyl, the arylalkylidene, the aryloxy, and the arylsulfanyl; the second cycloalkyl group, the cycloalkyl part of the (cycloalkyl)alkyl and the cycloalkylalkylidene; the heterocycle; and the heterocycle part of the (heterocycle)alkoxy, the (heterocycle)alkyl, and the (heterocycle)alkylidene can be further optionally substituted with one, two, or three substituents independently selected from the group consisting of alkoxy, alkyl, halo, haloalkoxy, haloalkyl, and hydroxy.

The term "cycloalkylalkoxy," as used herein, represents a cycloalkyl group attached to the parent molecular moiety through an alkoxy group.

The term "(cycloalkyl)alkyl," as used herein, represents a cycloalkyl group attached to the parent molecular moiety through an alkyl group.

The term "cycloalkylalkylidene," as used herein, represents a cycloalkyl group attached to the parent molecular moiety through an alkylidene group.

The term "cycloalkylcarbonyl," as used herein, represents a cycloalkyl group attached to the parent molecular moiety through a carbonyl group.

The term "cycloalkyloxy," as used herein, represents a cycloalkyl group attached to the parent molecular moiety through an oxygen atom.

The term "formyl," as used herein, represents —CHO.

The term "formylalkyl," as used herein, represents a formyl group attached to the parent molecular moiety through an alkyl group.

The term "halo," as used herein, represents F, Cl, Br, or I.

The term "haloalkoxy," as used herein, represents a haloalkyl group attached to the parent molecular moiety through an oxygen atom.

The term "haloalkyl," as used herein, represents an alkyl group substituted by one, two, three, or four halogen atoms.

The term "haloalkylcarbonyl," as used herein, represents a haloalkyl group attached to the parent molecular moiety through a carbonyl group.

The term "heteroalkenylene," as used herein, represents an unsaturated group of two to six atoms containing one or two heteroatoms independently selected from the group consisting of nitrogen, oxygen, and sulfur, wherein the remaining atoms are carbon. The heteroalkylene groups of the present invention can be attached to the parent molecular moiety through the carbon atoms or the heteroatoms in the chain.

The term "heteroalkylene," as used herein, represents a saturated group of two to six atoms containing one or two heteroatoms independently selected from the group consisting of nitrogen, oxygen, and sulfur, wherein the remaining atoms are carbon. The heteroalkylene groups of the present invention can be attached to the parent molecular moiety through the carbon atoms or the heteroatoms in the chain.

The term "heterocycle," as used herein, represents a monocyclic, bicyclic, or tricyclic ring system wherein one or more rings is a four-, five-, six-, or seven-membered ring containing one, two, or three heteroatoms independently selected from the group consisting of nitrogen, oxygen, and sulfur. Monocyclic ring systems are exemplified by any 3- or 4-membered ring containing a heteroatom independently selected from the group consisting of oxygen, nitrogen and sulfur; or a 5-, 6- or 7-membered ring containing one, two or three heteroatoms wherein the heteroatoms are independently selected from the group consisting of nitrogen, oxygen and sulfur. The 3- and 4-membered rings have no double bonds, the 5-membered ring has from 0–2 double bonds and the 6- and 7-membered rings have from 0–3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to phenyl ring, a monocyclic cycloalkyl group as defined herein, a monocyclic cycloalkenyl group, as defined herein, or another monocyclic heterocycle ring system. Representative examples of bicyclic ring systems include but are not limited to, benzimidazole, benzothiazole, benzothiophene, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, pyranopyridine, quinoline, quinolizine, quinoxaline, quinazoline, tetrahydroisoquinoline, tetrahydroquinoline, thiopyranopyridine, and the like. Tricyclic rings systems are exemplified by any of the above bicyclic ring systems fused to a phenyl ring, a monocyclic cycloalkyl group as defined herein, a monocyclic cycloalkenyl group as defined herein, or another monocyclic heterocycle ring system. Representative examples of tricyclic ring systems include, but are not limited to, acridine, carbazole, carboline, dibenzofuran, dibenzothiophene, naphthofuran, naphthothiophene, oxanthrene, phenazine, phenoxathiin, phenoxazine, phenothiazine, thianthrene, thioxanthene, xanthene, and the like. Heterocycle groups can be attached to the parent molecular moiety through a carbon atom or a nitrogen atom in the group.

The heterocycle groups of the present invention can be optionally substituted with one, two, three, four, or five substituents independently selected from the group consisting of alkenyl, alkoxy, alkoxyalkoxycarbonyl, alkoxyalkyl, alkoxycarbonyl, alkoxycarbonylalkyl, alkyl, alkylcarbonyl, alkylcarbonylalkyl, alkylcarbonyloxy, alkylsulfanylalkyl, alkynyl, amino, aminoalkyl, aminoalkylcarbonyl, aminocarbonyl, aminocarbonylalkyl, aminosulfonyl, aryl, arylalkenyl, arylalkoxyalkyl, arylalkoxyalkylcarbonyl, arylalkoxycarbonyl, arylalkyl, arylalkylcarbonyl, arylalkylsulfonyl, arylcarbonyl, aryloxy, aryloxyalkylcarbonyl, arylsulfanyl, arylsulfanylalkyl, arylsulfonyl, carboxy, cyano, cyanoalkyl, cycloalkyl, (cycloalkyl)alkyl, cycloalkylcarbonyl, formyl, formylalkyl, halo, haloalkoxy, haloalkyl, a second heterocycle, (heterocycle)alkenyl, (heterocycle)alkyl, (heterocycle)alkylcarbonyl, (heterocycle)alkylidene, heterocyclecarbonyl, heterocyclecarbonylalkyl, hydroxy, hydroxyalkyl, nitro, oxo, spirocycle, spiroheterocycle, and —C(NH)NH$_2$; wherein the aryl; the aryl part of the arylalkenyl, the arylalkoxyalkyl, the arylalkoxyalkylcarbonyl, the arylalkoxycarbonyl, the arylalkyl, the arylalkylcarbonyl, the arylalkylsulfonyl, the arylcarbonyl, the aryloxy, the aryloxyalkylcarbonyl, the arylsulfanyl, the arylsulfanylalkyl, and the arylsulfonyl; the heterocycle; and the heterocycle part of the (heterocycle)alkenyl, the (heterocycle)alkyl, the (heterocycle)alkylcarbonyl, the (heterocycle)alkylidene, the heterocyclecarbonyl, and the heterocyclecarbonylalkyl can be further optionally substituted with one, two, three, four, or five substituents independently selected from the group consisting of alkoxy, alkoxyalkoxycarbonyl, alkoxycarbonyl, alkyl, alkylcarbonyl, halo, haloalkoxy, haloalkyl, hydroxy, hydroxyalkyl, and nitro.

The term "(heterocycle)alkenyl," as used herein, represents an alkenyl group substituted by one, two, or three heterocycle groups. The alkenyl part of the (heterocycle) alkenyl can be optionally substituted with one or two aryl groups.

The term "(heterocycle)alkoxy," as used herein, represents a heterocycle group attached to the parent molecular moiety through an alkoxy group.

The term "(heterocycle)alkyl," as used herein, represents a heterocycle group attached to the parent molecular moiety through an alkyl group.

The term "(heterocycle)alkylcarbonyl," as used herein, represents a (heterocycle)alkyl group attached to the parent molecular moiety through a carbonyl group.

The term "(heterocycle)alkylidene," as used herein, represents a heterocycle group attached to the parent molecular moiety through an alkylidene group.

The term "heterocyclecarbonyl," as used herein, represents a heterocycle group attached to the parent molecular moiety through a carbonyl group.

The term "heterocyclecarbonylalkenyl," as used herein, represents a heterocyclecarbonyl group attached to the parent molecular moiety through an alkenyl group.

The term "heterocyclecarbonylalkyl," as used herein, represents a heterocyclecarbonyl group attached to the parent molecular moiety through an alkyl group:

The term "(heterocycle)oxy," as used herein, represents a heterocycle group attached to the parent molecular moiety through an oxygen atom.

The term "(heterocycle)sulfanyl," as used herein, represents a heterocycle group attached to the parent molecular moiety through a sulfur atom.

The term "(heterocycle)sulfanylalkyl," as used herein, represents a heterocyclesulfanyl group attached to the parent molecular moiety through an alkyl group.

The term "hydroxy," as used herein, represents —OH.

The term "hydroxyalkyl," as used herein, represents a hydroxy group attached to the parent molecular moiety through an alkyl group.

The term "nitro," as used herein, represents —NO$_2$.

The term "nitrogen protecting group," as used herein, represents groups intended to protect an amino group against undesirable reactions during synthetic procedures. Common N-protecting groups comprise acyl groups such as acetyl, benzoyl, 2-bromoacetyl, 4-bromobenzoyl, tert-butylacetyl, carboxaldehyde, 2-chloroacetyl, 4-chlorobenzoyl, a-chlorobutyryl, 4-nitrobenzoyl, o-nitrophenoxyacetyl, phthalyl, pivaloyl, propionyl, trichloroacetyl, and trifluoroacetyl; sulfonyl groups such as benzenesulfonyl, and p-toluenesulfonyl; carbamate forming groups such as benzyloxycarbonyl, benzyloxycarbonyl (Cbz), tert-butyloxycarbonyl (Boc), p-chlorobenzyloxycarbonyl, p-methoxybenzyloxycarbonyl, and the like.

The term "oxo," as used herein, represents (=O).

The term "spirocycle," as used herein, represents an alkenylene or alkylene group in which both ends of the alkenylene or alkylene group are attached to the same carbon of the parent molecular moiety to form a bicyclic group. The spirocycle groups of the present invention can be optionally substituted with one substituent selected from the group consisting of alkyl, aryl, arylalkoxyalkyl, arylalkyl, and aryloxyalkyl.

The term "spiroheterocycle," as used herein, represents a heteroalkenylene or heteroalkylene group in which both ends of the heteroalkenylene or heteroalkylene group are attached to the same carbon of the parent molecular moiety to form a bicyclic group. The spiroheterocycle groups of the present invention can be optionally substituted with one substituent selected from the group consisting of alkyl, aryl, arylalkoxyalkyl, arylalkyl, and aryloxyalkyl.

The term "sulfinyl," as used herein, represents —S(O)—.

The term "sulfonyl," as used herein, represents —SO$_2$—.

The term "therapeutically acceptable salt," as use herein, represents those salts which are, within the scope of sound medical judgment, suitable for use in contact with the tissues of humans and lower animals without undue toxicity, irritation, allergic response and the like and are commensurate with a reasonable benefit/risk ratio. The salts can be prepared in situ during the final isolation and purification of the compounds of the present invention or separately by reacting a free base group with a suitable organic acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, trifluoroacetate, undecanoate, valerate salts, and the like. Representative alkali or alkaline earth metal salts include calcium, lithium, magnesium, potassium, sodium, and the like, as well as non-toxic ammonium, quaternary ammonium, and amine cations, including, but not limited to, ammonium, dimethylamine, ethylamine, methylamine, tetraethylammonium, tetramethylammonium, triethylamine, trimethylamine, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

The present compounds can also exist as therapeutically acceptable prodrugs. The term "therapeutically acceptable prodrug," refers to those prodrugs or zwitterions which are suitable for use in contact with the tissues of patients without undue toxicity, irritation, and allergic response, are commensurate with a reasonable benefit/risk ratio, and are effective for their intended use. The term "prodrug," refers to compounds which are rapidly transformed in vivo to parent compounds of formula (I) for example, by hydrolysis in blood.

Asymmetric centers exist in the compounds of the present invention. These centers are designated by the symbols "R" or "S," depending on the configuration of substituents around the chiral carbon atom. It should be understood that the invention encompasses all stereochemical isomeric forms, or mixtures thereof, which possess the ability to induce apoptosis. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, or direct separation of enantiomers on chiral chromatographic columns. Starting compounds of particular stereochemistry are either commercially available or can be made and resolved by techniques known in the art.

According to methods of treatment, the compounds of the present invention can be useful for the prevention of metastases from the tumors described above either when used alone or in combination with radiotherapy and/or other chemotherapeutic treatments conventionally administered to patients for treating cancer. When using the compounds of the present invention for chemotherapy, the specific therapeutically effective dose level for any particular patient will depend upon factors such as the disorder being treated and the severity of the disorder; the activity of the particular compound used; the specific composition employed; the age, body weight, general health, sex, and diet of the patient; the time of administration; the route of administration; the rate of excretion of the compound employed; the duration of treatment; and drugs used in combination with or coincidently with the compound used. For example, when used in the treatment of solid tumors, compounds of the present invention can be administered with chemotherapeutic agents such as alpha inteferon, COMP (cyclophosphamide, vincristine, methotrexate, and prednisone), etoposide, mBACOD (methortrexate, bleomycin, doxorubicin, cyclophosphamide, vincristine, and dexamethasone), PRO-MACE/MOPP (prednisone, methotrexate (w/leucovin rescue), doxorubicin, cyclophosphamide, taxol, etoposide/mechlorethamine, vincristine, prednisone, and procarbazine), vincristine, vinblastine, angioinhibins, TNP-470, pentosan polysulfate, platelet factor 4, angiostatin, LM-609, SU-101, CM-101, Techgalan, thalidomide, SP-PG, and the like. For example, a tumor may be treated conventionally with surgery, radiation or chemotherapy and a compound of the present invention subsequently administered to extend the dormancy of micrometastases and to stabilize and inhibit the growth of any residual primary tumor.

The compounds of the present invention can be administered orally, parenterally, osmotically (nasal sprays), rectally, vaginally, or topically in unit dosage formulations containing carriers, adjuvants, diluents, vehicles, or combinations thereof. The term "parenteral" includes infusion as well as subcutaneous, intravenous, intramuscular, and intrasternal injection.

Parenterally administered aqueous or oleaginous suspensions of the compounds of the present invention can be formulated with dispersing, wetting, or suspending agents. The injectable preparation can also be an injectable solution or suspension in a diluent or solvent. Among the acceptable diluents or solvents employed are water, saline, Ringer's solution, buffers, dilute acids or bases, dilute amino acid solutions, monoglycerides, diglycerides, fatty acids such as oleic acid, and fixed oils such as monoglycerides or diglycerides.

The chemotherapeutic effect of parenterally administered compounds can be prolonged by slowing their absorption. One way to slow the absorption of a particular compound is administering injectable depot forms comprising suspensions of crystalline, amorphous, or otherwise water-insoluble forms of the compound. The rate of absorption of the compound is dependent on its rate of dissolution which is, in turn, dependent on its physical state. Another way to slow absorption of a particular compound is administering injectable depot forms comprising the compound as an oleaginous solution or suspension. Yet another way to slow absorption of a particular compound is administering injectable depot forms comprising microcapsule matrices of the compound trapped within liposomes, microemulsions, or biodegradable polymers such as polylactide-polyglycolide, polyorthoesters or polyanhydrides. Depending on the ratio of drug to polymer and the composition of the polymer, the rate of drug release can be controlled.

Transdermal patches also provide controlled delivery of the compounds. The rate of absorption can be slowed by using rate controlling membranes or by trapping the compound within a polymer matrix or gel. Conversely, absorption enhancers can be used to increase absorption.

Solid dosage forms for oral administration include capsules, tablets, pills, powders, and granules.) In these solid dosage forms, the active compound can optionally comprise diluents such as sucrose, lactose, starch, talc, silicic acid, aluminum hydroxide, calcium silicates, polyamide powder, tableting lubricants, and tableting aids such as magnesium stearate or microcrystalline cellulose. Capsules, tablets and pills can also comprise buffering agents; and tablets and pills can be prepared with enteric coatings or other release-controlling coatings. Powders and sprays can also contain excipients such as talc, silicic acid, aluminum hydroxide, calcium silicate, polyamide powder, or mixtures thereof. Sprays can additionally contain customary propellants such as chlorofluorohydrocarbons or substitutes thereof.

Liquid dosage forms for oral administration include emulsions, microemulsions, solutions, suspensions, syrups, and elixirs comprising inert diluents such as water. These compositions can also comprise adjuvants such as wetting, emulsifying, suspending, sweetening, flavoring, and perfuming agents.

Topical dosage forms include ointments, pastes, creams, lotions, gels, powders, solutions, sprays, inhalants, and transdermal patches. The compound is mixed under sterile conditions with a carrier and any needed preservatives or buffers. These dosage forms can also include excipients such as animal and vegetable fats, oils, waxes, paraffins, starch, tragacanth, cellulose derivatives, polyethylene glycols, silicones, bentonites, silicic acid, talc and zinc oxide, or mixtures thereof. Suppositories for rectal or vaginal administration can be prepared by mixing the compounds of the present invention with a suitable nonirritating excipient such as cocoa butter or polyethylene glycol, each of which is solid at ordinary temperature but fluid in the rectum or vagina. Ophthalmic formulations comprising eye drops, eye ointments, powders, and solutions are also contemplated as being within the scope of the present invention.

The total daily dose of the compounds of the present invention administered to a host in single or divided doses can be in amounts from about 0.1 to about 200 mg/kg body weight or preferably from about 0.25 to about 100 mg/kg body weight. Single dose compositions can contain these amounts or submultiples thereof to make up the daily dose.

Determination of Biological Activity

Assays for the inhibition of Bcl-$X_L$ were performed in 96-well microtiter plates. Compounds of the present invention were diluted in DMSO to concentrations between 100 μM and 1 pM and introduced into each cell of the plate. A mixture totaling 125 μL per well of assay buffer (20 mM phosphate buffer (pH 7.4), 1 mM EDTA, 0.05% PEG-8000), 50 nM of BCL-$X_L$ protein (prepared according to the procedure described in Science 1997, 275, 983–986), 5 nM fluorescein-labeled BAD peptide (purchased from Synpep, Calif.), and the DMSO solution of the compound of the present invention was shaken for 2 minutes and placed in a LJL Analyst (LJL Bio Systems, CA). A negative control (DMSO, 5 nM BAD peptide, assay buffer) and a positive control (DMSO, 5 nM BAD peptide, 50 nM BCL-$X_L$, assay buffer) were used to determine the range of the assay. Polarization was measured at room temperature using a continuous Fluorescein lamp (excitation 485 mM, emission 530 mM). Percentage of inhibition was determined by (1-((mP value of well-negative control)/range))×100%. $IC_{50}$ values were calculated using Microsoft Excel. Compounds of the present invention have $IC_{50}$ values between 0.011 and 10 μM and are therefore useful for inhibiting BCL-$X_L$ and treating apoptosis-mediated diseases. Preferred compounds of the present invention have $IC_{50}$ values between 0.011 and 0.5 μM, and most preferred compounds have IC50 values between 0.011 and 0.10 μM.

Assays for the inhibition of Bcl-2 were performed in 96-well microtiter plates. Compounds of the instant invention were diluted in DMSO to concentrations between 100 μM and 1 pM and introduced into each well of the plate. A mixture totaling 125 μL per well of assay buffer (20 mM phosphate buffer (pH 7.4), 1 mM EDTA, 0.05% PF-68), 30 nM of Bcl-2 protein (prepared according to the procedure described in PNAS 2001, 98, 3012–3017), 5 nM fluorescein-labeled BAX peptide (prepared in-house), and the DMSO solution of the compound of the instant invention was shaken for 2 minutes and placed in a LJL Analyst (LJL Bio Systems, CA). A negative control (DMSO, 5 nM BAX peptide, assay buffer) and a positive control (DMSO, 5 nM BAX peptide, 30 nM Bcl-2, assay buffer) were used to determine the range of the assay. Polarization was measured at room temperature using a continuous Fluorescein lamp (excitation 485 mM, emission 530 mM). Percentage of inhibition was determined by (1-((mP value of well-negative control)/range))×100%. $IC_{50}$ values were calculated using Microsoft Excel. Compounds of the present invention have $IC_{50}$ values between 0.102 and 10 μM and are therefore useful for inhibiting Bcl-2 and treating apoptosis-mediated diseases. Preferred compounds of the present invention have $IC_{50}$ values between 0.102 and 0.5 μM, and most preferred compounds have IC50 values between 0.102 and 0.0.25 μM.

Based upon the structural and functional similarity of the Bcl antiapoptotic proteins, it is reasonable to expect that in addition to inducing apoptosis by the inhibition of Bcl-$X_L$ and Bcl-2, the current invention may induce apoptosis through their action on other antiapoptotic proteins in the Bcl family of proteins, such as Bcl-w, Bcl-b, MCL-1 and/or A1/Bfl-1.

Synthetic Methods

Abbreviations which have been used in the descriptions of the scheme and the examples that follow are: DEAD for diethyl azodicarboxylate; DIAD for diisopropyl azodicarboxylate; $PPh_3$ for triphenylphosphine; BOC for tert-butoxycarbonyl; DMAP for 4-dimethylaminopyridine; EDCI for 1-(3-dimethylaminopropyl)-3-ethylcarbodiimide; THF for tetrahydrofuran; TFA for trifluoroacetic acid; DMSO for dimethylsulfoxide; dba for dibenzylideneacetone; OAc for acetate; and $P(t-Bu)_3$ for tri-tert-butylphosphine.

The compounds and processes of the present invention will be better understood in connection with the following synthetic schemes which illustrate the methods by which the compounds of the invention may be prepared. Starting materials can be obtained from commercial sources or prepared by well-established literature methods known to those of ordinary skill in the art. It will be readily apparent to one of ordinary skill in the art that the compounds defined above can be synthesized by substitution of the appropriate reactants and agents in the syntheses shown below. The groups $R^1$, $R^2$, $R^3$, $R^4$, and $R^{15}$ are as defined above unless otherwise noted below. It will be readily apparent to one skilled in the art that the selective protection and deprotections steps, as well as the order of the steps themselves, can be carried out in varying order, depending on the nature of $R^1$, $R^2$, $R^3$, $R^4$, $R^{15}$, $R^a$, $R^b$, and $R^c$, to successfully complete the syntheses shown below.

This invention is intended to encompass compounds having formula (I) when prepared by synthetic processes or by metabolic processes. Preparation of the compounds of the invention by metabolic processes include those occurring in the human or animal body (in vivo) or processes occurring in vitro.

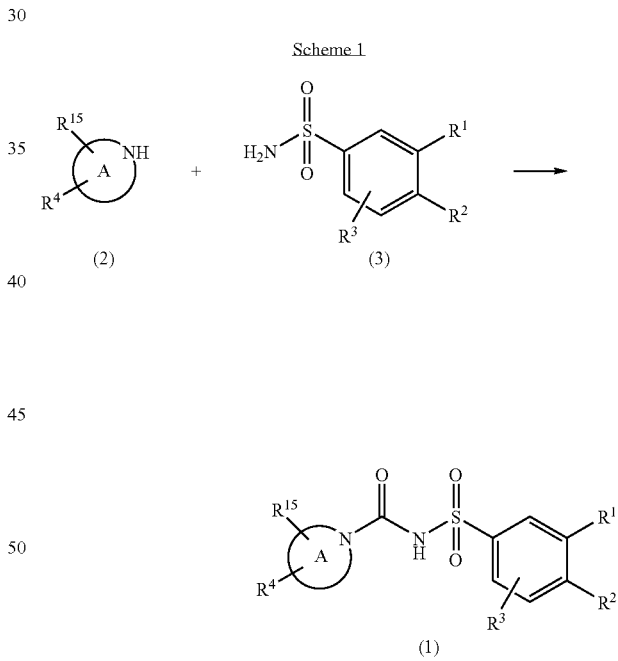

As shown in Scheme 1, compounds of formula (2) (which can be prepared according to the procedures described in the schemes and examples listed below) can be reacted with compounds of formula (3) (which can be prepared according to the procedures described in Schemes 2, 3, and 1 1, or by the procedure described in commonly owned U.S. patent application Ser. No. 09/957,256, filed Sep. 20, 2001) in the presence of a base such as triethylamine, or diisopropyl-ethylamine; and an an activated carbonyl species such as triphosgene, p-nitrophenylchloroformate or 1,1'-carbonyldiimidazole to provide compounds of formula (I).

Scheme 2

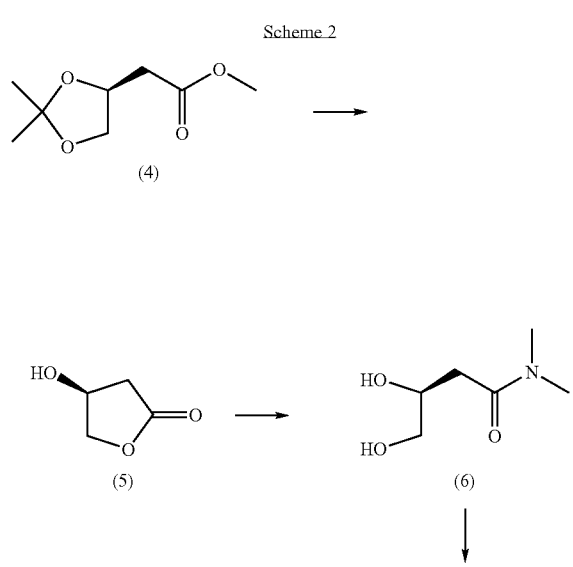

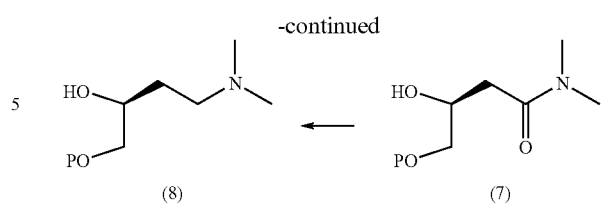

Scheme 2 shows the synthesis of compounds of formula (8). Compounds of formula (4) can be converted to compounds of formula (5) by treatment with an acid such as p-toluenesulfonic acid or trifluoroacetic acid. Compounds of formula (5) can be treated with dimethylamine to provide compounds of formula (6) which can be protected with a group that is selective for the primary alcohol (such as a p-methoxybenzyl; formed by treatment of compounds of formula (6) with 4-methoxybenzyl 2,2,2-trichloroethanimidoate in the presence of an acid such as trifluoroacetic acid; or prepared by other methods capable of adding a p-methoxybenzyl protecting group) to provide compounds of formula (7). Compounds of formula (7) can be treated with a reducing agent such as borane, sodium borohydride, or lithium aluminum hydride to provide compounds of formula (8).

Scheme 3

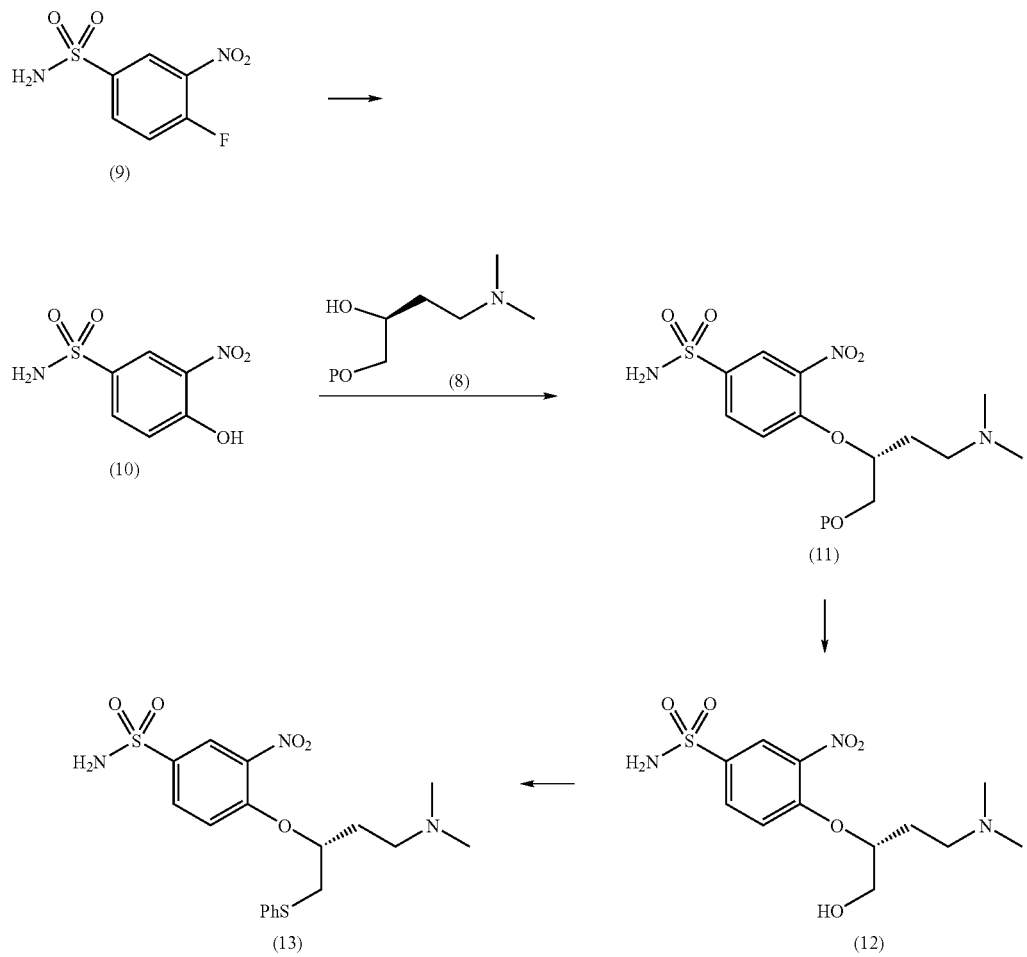

As shown in Scheme 3, compounds of formula (9) can be converted to compounds of formula (10) by treatment with sodium hydroxide. Condensation of compounds of formula (10) with compounds of formula (8) in the presence of triphenylphosphine and DEAD or DIAD provides compounds of formula (11) which can be deprotected under conditions known to those of ordinary skill in the art (for example, using aqueous HCl if P is p-methoxybenzyl) to provide compounds of formula (12). Treatment with compounds of formula (12) with diphenyldisulfide in the presence of tributylphosphine provides compounds of formula (13) which can be converted to compounds of formula (I) by the method shown in Scheme 1.

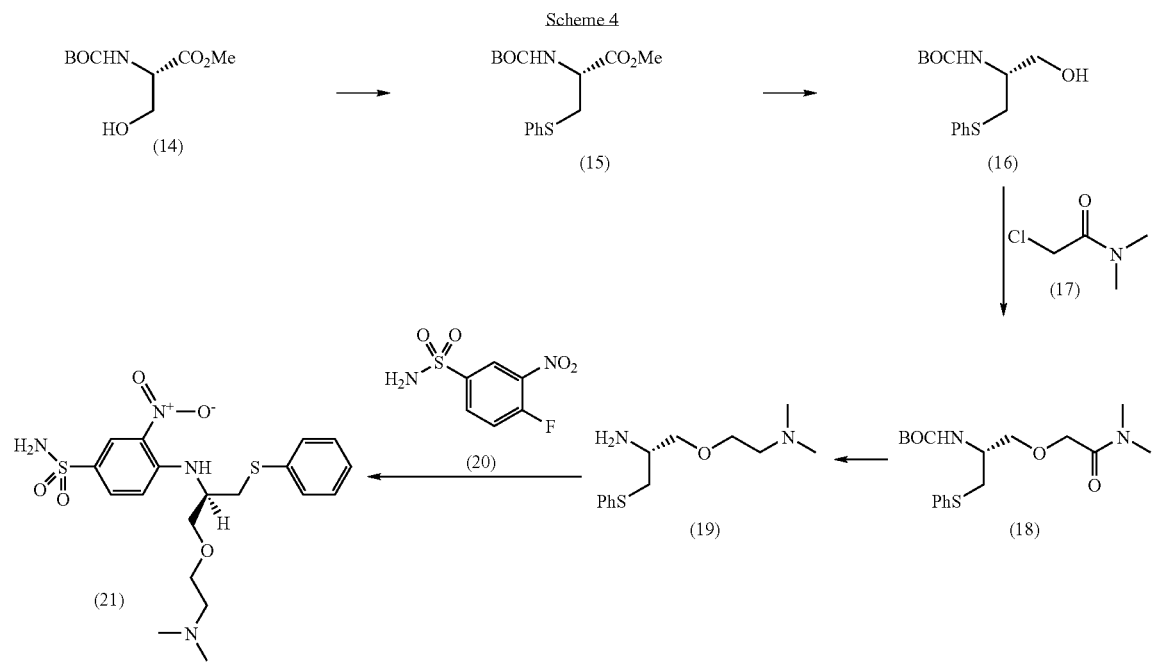

Scheme 4 shows the synthesis of compounds of formula (21). Compounds of formula (14) can be converted to compounds of formula (15) by converting the hydroxy group to a leaving group (such as a tosylate or mesylate group; formed by treatment with p-toluenesulfonyl chloride or methanesulfonyl chloride, respectively, in the presence of a base such as triethylamine or diisopropylethylamine) and treating the resulting product with thiophenol in the presence of a base such as triethylamine or diisopropylethylamine. Compounds of formula (15) can be reduced to compounds of formula (16) by treatment with a reducing agent such as diisobutylaluminum hydride. Condensation of compounds of formula (16) with compounds of formula (17) in the presence of a base such as sodium hydride provides compounds of formula (18) which can be reduced in the presence of a reducing agent such as borane or sodium borohydride, then deprotected under conditions known to those of ordinary skill in the art (such as treatment with trifluoroacetic acid) to provide compounds of formula (19). Compounds of formula (19) can be reacted with compounds of formula (20) in the presence of a base such as diisopropylethylamine or triethylamine to provide compounds of formula (21), which can be converted to compounds of formula (I) under the conditions described in Scheme 1.

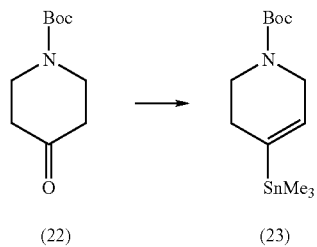

As shown in Scheme 5, compounds of formula (23) can be prepared by treating compounds of formula (22) with a base such as lithium hexamethyldisilazide or lithium diisopropylamine and then treating the resulting anion with N-phenyltrifluoromethanesulfonimide to provide the vinyl triflate, which can then be coupled with hexamethylditin in the presence of a palladium catalyst such as $(PPh_3)_4Pd$ or $PdCl_2(PPh_3)_2$ to provide the desired product.

Scheme 6

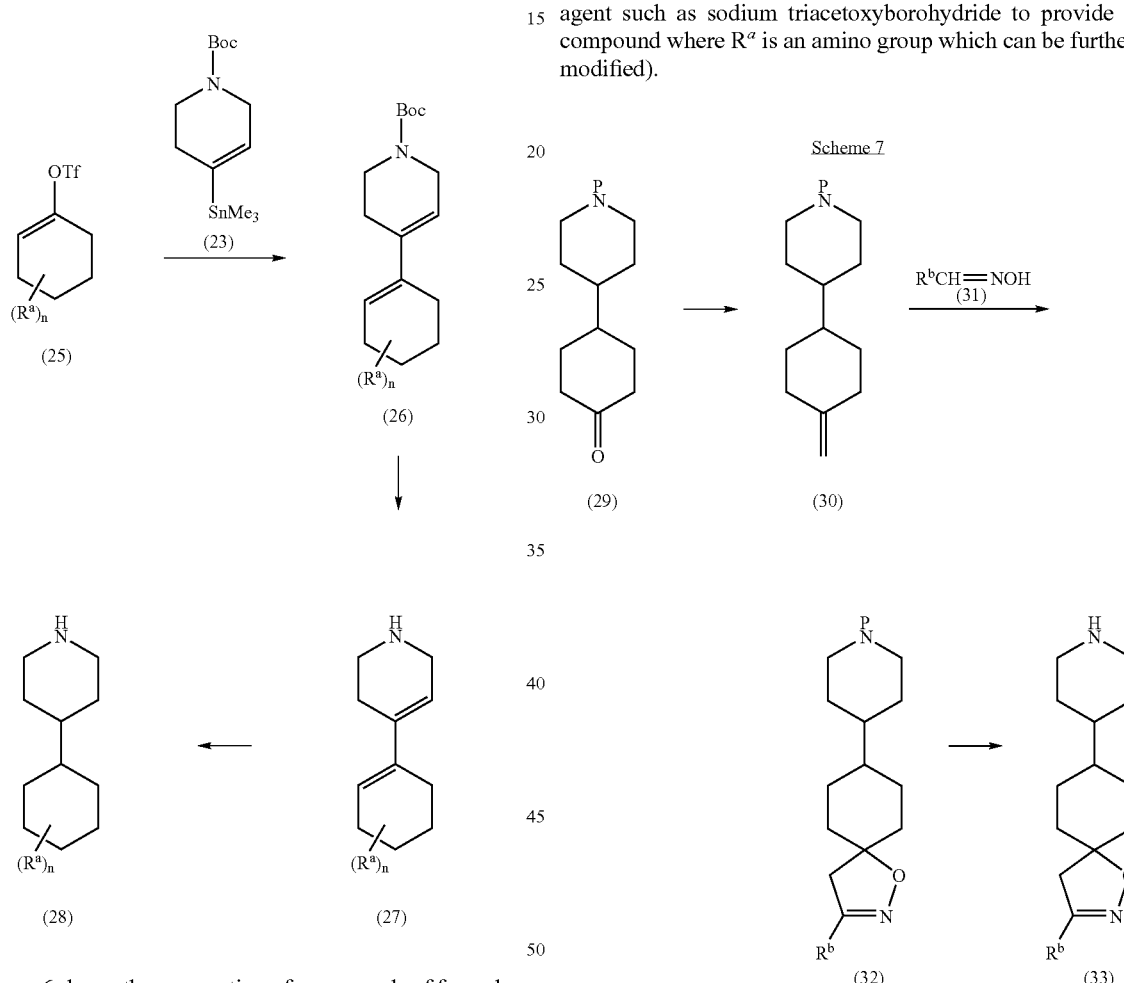

Scheme 6 shows the preparation of compounds of formula (28). Compounds of formula (24) (where n is 0 to 5 and each $R^a$ is independently selected from the list of substituents included in the definition of cycloalkyl) can be treated with a base such as lithium diisopropylamide or lithium hexamethyldisilazide and then quenched with trifluoromethane sulfonic anhydride or N-phenyltrifluoromethanesulfonimide to provide compounds of formula (25). Compounds of formula (25) can be coupled with compounds of formula (23) in the presence of a palladium catalyst such as (PPh$_3$)$_4$Pd or PdCl$_2$(PPh$_3$)$_2$ to provide compounds of formula (26). Compounds of formula (26) can be deprotected under conditions known to those of ordinary skill in the art (such as hydrochloric acid or trifluoroacetic acid) to provide compounds of formula (27) which can be hydrogenated in the presence of a catalyst such as palladium on carbon to provide compounds of formula (28). Compounds of formula (28) can be converted to compounds of formula (I) under the conditions described in Scheme 1.

Each $R^a$ can be converted to an alternative $R^a$ at various points in the synthesis (i.e., before or after removal of the BOC protecting group depending on the nature of the modifiation) by methods known to those of ordinary skill in the art. For example, if $R^a$ is an oxo group (=O) it can be reacted with a Wittig reagent (RCH$_2$PPh$_3$Br, where R is an alkyl group) to provide the tri-substituted double bond. The double bond can be hydrogenated to provide compounds where $R^a$ is alkyl. In another example, if $R^a$ is an oxo group, it can be reacted with an amine in the presence of a reducing agent such as sodium triacetoxyborohydride to provide a compound where $R^a$ is an amino group which can be further modified).

Scheme 7

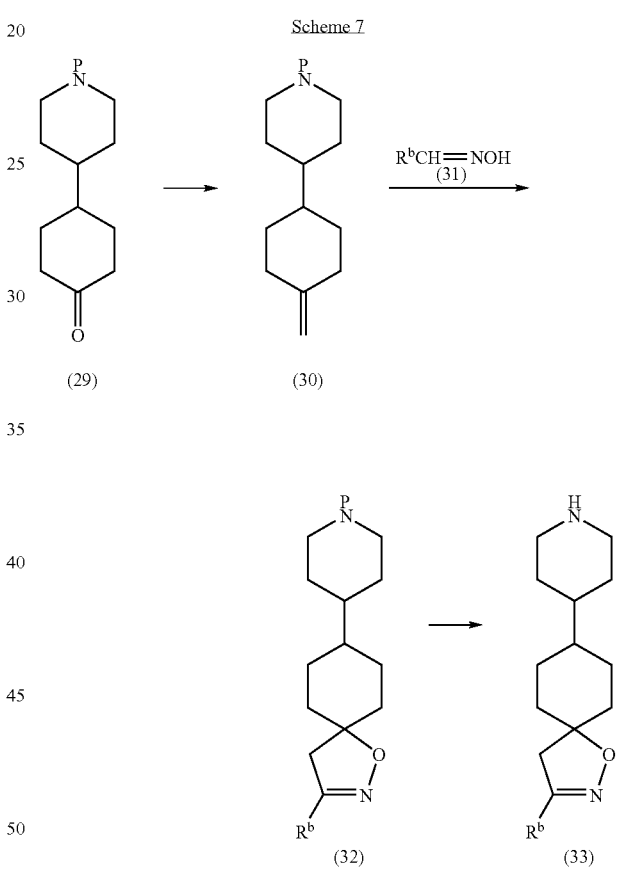

The preparation of compounds of formula (33) is shown in Scheme 7. Compounds of formula (29) (P is a nitrogen protecting group such as benzyl; prepared according to a procedure similar to that described in Scheme 6) can be treated with CH$_2$(PPh$_3$)I and butyllithium to provide compounds of formula (30). Treatment of compounds of formula (30) with compounds of formula (31) (where $R^b$ is alkyl) in the presence of sodium hypochlorite to provide compounds of formula (32). Deprotection of the nitrogen can be accomplished under conditions known to those of ordinary skill in the art (for example, using α-chloroethyl chloroformate to remove a benzyl group) to provide compounds of formula (33), which can be converted to compounds of formula (I) using the procedure outlined in Scheme 1.

Scheme 8

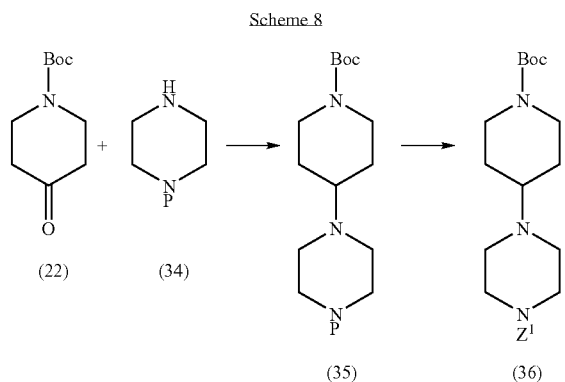

Scheme 8 shows the synthesis of compounds of formula (36). Compounds of formula (22) can be reated with compounds of formula (34) (P is a protecting group such as benzyl) in the presence of a reducing agent such as sodium triacetoxyborohydride to provide compounds of formula (35). Compounds of formula (35) can be converted to compounds of formula (36) ($Z^1$ is hydrogen) by methods known to those of ordinary skill in the art (for example, using α-chloroethyl chloroformate to remove a benzyl group). Compounds of formula (36) where $Z^1$ is hydrogen can be reacted with a variety of agents such as acid chlorides, aldehydes, and sulfonyl chlorides under conditions known to those of ordinary skill in the art to provide compounds of formula (36) where $Z^1$ is alkylcarbonyl, alkyl, or alkylsuflonyl. Deprotection of the BOC group in compounds of formula (36) (for example, with trifluoracetic acid) provides the free amine which can then be subjected to the conditions described in Scheme 1 to provide compounds of formula (I).

Scheme 9

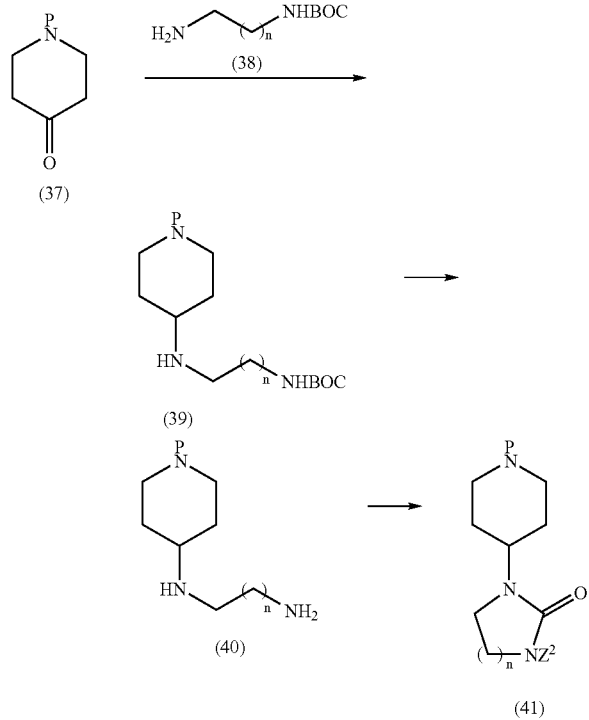

Compounds of formula (41) can be prepared following the synthesis shown in Scheme 9. Compounds of formula (37) (P is a nitrogen protecting group such as benzyl) can be treated with compounds of formula (38) (n is 1 or 2) in the presence of a reducing agent such as sodium triacetoxyborohydride to provide compounds of formula (39). Removal of the BOC group under conditions known to those of ordinary skill in the art (for example, trifluoroacetic acid) provides compounds of formula (40) which can be reacted with a reagent such as triphosgene or 1,1'-carbonyldiimidazole to provide compounds of formula (41) where $Z^2$ is hydrogen. Compounds of formula (41) where $Z^2$ is hydrogen can be treated with groups such as alkyl halides to provide compounds of formula (41) where $Z^2$ is a group such as alkyl, arylalkyl, or cycloalkylalkyl. Removal of the protecting group (P) under conditions known to those of ordinary skill in the art (for example, using α-chloroethyl chloroformate to remove a benzyl group) provides the free amine which can be reacted under the conditions described in Scheme 1 to provide compounds of formula (I).

Scheme 10

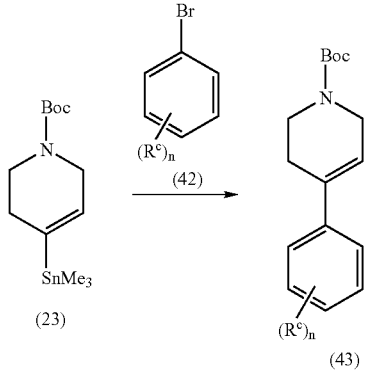

Compounds of formula (43) (n is 0, 1, 2, 3, 4, or 5; and each $R^c$ is independently selected from the group of substituents listed under the definition of aryl) can be prepared by reacting compounds of formula (23) (prepared according to the procedure described in Scheme 5) can be coupled with compounds of formula (42) in the presence of a palladium catalyst such as Pd(PPh$_3$)$_4$ or PdCl$_2$(PPh$_3$)$_2$ to provide compounds of formula (43). The double bond can optionally be hydrogenated as shown in Scheme 6. Removal of the BOC group by conditions known to those of ordinary skill in the art (for example, trifluoroacetic acid) provides the free amine which can be reacted under the conditions described in Scheme 1 to provide compounds of formula (I).

Each $R^c$ can be modified either before or after removal of the protecting group (depending on the modification being carried out) to provide alternative $R^c$ groups. For example, if $R^c$ is nitro, the nitro group can be reduced to a primary amino group using conditions known to those of ordinary skill in the art. The primary amino group thus formed can be treated with an acid chloride to provide an amide or with an aldehyde under reductive amination conditions to provide an alkyl substituted amine.

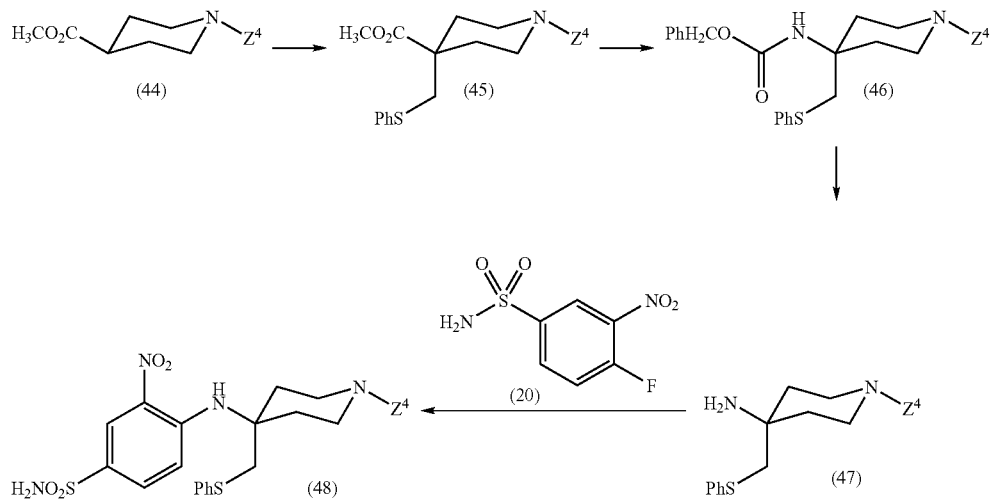

Scheme 11

Scheme 11 shows the synthesis of compounds of formula (48). Compounds of formula (44) ($Z^4$ is BOC or $CH_3$) can be treated with a strong base such as lithium diisopropylamide or lithium hexamethyldisilazide then treated with chloromethyl phenyl sulfide to provide compounds of formula (45) ($Z^4$ is BOC or $CH_3$). Coversion of compounds of formula (45) to compounds of formula (46) ($Z^4$ is BOC or $CH_3$) can be accomplished by treatment with diphenyl azidophosphate and benzyl alcohol. Treatment of compounds of formula (46) with sodium methanethiolate provides compounds of formula (47) ($Z^4$ is BOC or $CH_3$). Compounds of formula (47) ($Z^4$ is BOC or $CH_3$) can be reacted with compounds of formula (20) to provide compounds of formula (48) ($Z^4$ is BOC or $CH_3$). Compounds of formula (48) where $Z^4$ is BOC can be converted to compounds of formula (48) where $Z^4$ is hydrogen by deprotection using conditions known to those of ordinary skill in the art (for example, trifluoroacetic acid). Compounds of formula (48) ($Z^4$ is hydrogen or $CH_3$) can be converted to compounds of formula (I) under the conditions described in Scheme 1.

The present invention will now be described in connection with certain preferred embodiments which are not intended to limit its scope. On the contrary, the present invention covers all alternatives, modifications, and equivalents as can be included within the scope of the claims. Thus, the following examples, which include preferred embodiments, will illustrate the preferred practice of the present invention, it being understood that the examples are for the purposes of illustration of certain preferred embodiments and are presented to provide what is believed to be the most useful and readily understood description of its procedures and conceptual aspects.

Compounds of the invention were named by ACD/ChemSketch version 5.0 (developed by Advanced Chemistry Development, Inc., Toronto, ON, Canada) or were given names which appeared to be consistent with ACD nomenclature.

EXAMPLE 1

N-{[4-({(1R)-3-(dimethylamino)-1-[(phenylthio)methyl]propyl}amino)-3-nitrophenyl]sulfonyl}-4-phenylpiperazine-1-carboxamide A solution of N-phenylpiperazine (30 mg, 0.185 mmol) in dichloromethane (2 mL) was treated with triethylamine (77 μL, 0.555 mmol), cooled to 0° C., treated with triphosgene (33 mg, 0.111 mmol), warmed to room temperature, stirred for 1 hour, treated with 4-({(1R)-3-(dimethylamino)-1-[(phenylthio)methyl]propyl}amino)-3-nitrobenzenesulfonamide (prepared according to the procedure described in commonly owned U.S. patent application Ser. No. 09/957,256, filed Sep. 20, 2001, 86 mg, 0.204 mmol) and DMAP (23 mg, 0.185 mmol), stirred overnight, and concentrated. The concentrate was purified by flash column chromatography on silica gel with 20% 2N $NH_3$ in methanol/dichloromethaneto provide the desired product (46 mg, 41%). MS (ESI) m/e 613 (M+H)$^+$; $^1$H NMR (500 MHz, $CD_3OD$) δ 8.0–6.75 (13H, m), 4.15 (1H, m), 3.59 (2H, t), 3.39 (4H, m), 3.25 (4H, m), 3.16 (2H, t), 2.88 (6H, s), 2.35–2.15 (2H, m).

EXAMPLE 2

N-{[4-({(1R)-3-(dimethylamino)-1-[(phenylthio)methyl]propyl}amino)-3-nitrophenyl]sulfonyl}-4-(4-nitrophenyl)piperazine-1-carboxamide A solution of 4-({(1R)-3-(dimethylamino)-1-[(phenylthio)methyl]propyl}amino)-3-nitrobenzenesulfonamide (prepared according to the procedure described in commonly owned U.S. patent application Ser. No. 09/957,256, filed Sep. 20, 2001, 60 mg, 0.142 mmol) in dichloromethane (2 mL) at room temperature was treated with triethylamine (59 μL, 0.426 mmol) and p-nitrophenyl chloroformate (31 mg, 0.156 mmol), stirred for 2 hours, treated with 1-(4-nitrophenyl)-piperazine (35 mg, 0.169 mmol) and DMAP (17 mg, 0.142 mmol), stirred overnight, and concentrated. The concentrate was purified by flash column chromatography on silica gel with 20% 2N $NH_3$ in methanol/dichloromethane) to provide the desired product (40 mg, 43%). MS (ESI) m/e 658 (M+H)$^+$; $^1$H NMR (500 MHz, $CD_3OD$)

δ 8.5–6.75 (12H, m), 4.16 (1H, m), 3.69 (2H, t), 3.59 (2H, br s), 3.47 (2H. br s), 3.37 (2H, br d), 3.24 (4H, m), 2.87 (6H, s), 2.35–2.15 (2H, m).

EXAMPLE 3

4-[4-(benzyloxy)phenyl]-N-{[4-({(1R)-3-(dimethylamino)-1-[(phenylthio)methyl]propyl}amino)-3-nitrophenyl]sulfonyl}piperazine-1-carboxamide The desired product was prepared by substituting 1-(4-benzyloxyphenyl)-piperazine for N-phenylpiperazine in Example 1. MS (ESI) m/e 719 (M+H)$^+$; $^1$H NMR (500 MHz, CD$_3$OD) δ 8.0–6.75 (17H, m), 5.05 (2H, s), 4.18 (1H, m), 3.66 (2H, t), 3.43–3.19 (10H, m), 2.88 (6H, s), 2.40–2.10 (2H, m).

EXAMPLE 4

N-{[4-({(1R)-3-(dimethylamino)-1-[(phenylthio)methyl]propyl}amino)-3-nitrophenyl]sulfonyl}-4-[4-(3-morpholin-4-yl-3-oxopropyl)phenyl]piperazine-1-carboxamide

EXAMPLE 4A

4-[(2E)-3-(4-bromophenyl)prop-2-enoyl]morpholine

A solution of cinnamic acid (1 g, 4.405 mmol) in dichloromethane (50 mL) at room temperature was treated with morpholine (422 μL, 4.846 mmol), EDCI (1.015 g, 5.286 mmol), and DMAP (54 mg, 0.441 mmol), stirred overnight, and partitioned between ethyl acetate and saturated NH$_4$Cl. The aqueous layer was extracted with ethyl acetate (3×50 mL) and the combined extracts were washed with brine and dried (MgSO$_4$), filtered, and concentrated to provide the desired product.

EXAMPLE 4B

4-[3-(4-bromophenyl)propanoyl]morpholine

A solution of Example 4A (4.405 mmol) in 1:1 ethyl acetate/ethanol (50 mL) was treated with Wilkinson's catalyst (815 mg, 0.880 mmol), degassed three times by freeze-thaw cycle, heated to reflux under nitrogen atmosphere for 2 days, and cooled to room temperature. The solution was adsorbed onto silica gel and purified by flash column chromatography with 50% ethyl acetate in hexane to provide the desired product (1.024 g, 78%). $^1$H NMR (300 MHz, CD$_3$OD) δ 7.40 (2H, d), 7.10 (2H, d), 3.62 (4H, m), 3.57 (2H, t), 3.38 (2H, t), 2.94 (2H, t), 2.58 (2H, t).

EXAMPLE 4C tert-butyl 4-[4-(3-morpholin-4-yl-3-oxopropyl)phenyl]piperazine-1-carboxylate A solution of Example 4B (400 mg, 1.342 mmol) in toluene (3.4 mL) at room temperature was treated with 1-tert-butoxycarbonylpiperazine (300 mg, 1.611 mmol), Pd$_2$(dba)$_3$ (61 mg, 0.0671 mmol), bis-tert-butyl biphenylphosphine (40 mg, 0.134 mmol) and sodium tert-butoxide (199 mg, 2.013 mmol), degassed three times by freeze-thaw cycle, stirred overnight and partitioned between ethyl acetate and saturated NH$_4$Cl. The aqueous layer was extracted with ethyl acetate (3×30 mL) and the combined extracts were dried (MgSO$_4$), filtered, and concentrated. The concentrate was purified by flash column chromatography on silica gel with 66% acetonitrile in dichloromethane to provide the desired product (317 mg, 59%). $^1$H NMR (300 MHz, CD$_3$OD) δ 7.12 (2H, m), 6.91 (2H, br), 3.63 (8H, br), 3.53 (2H, t), 3.36 (2H, t), 3.10 (4H, br), 2.91 (2H, t), 2.58 (1H, t), 1.48 (9H, s).

EXAMPLE 4D

4-[3-(4-piperazin-1-ylphenyl)propanoyl]morpholine dihydrochloride

A mixture of Example 4C (317 mg, 0.787 mmol) in 4N HCl/dioxane was allowed to stand for 1 hour and concentrated to provide the desired product.

EXAMPLE 4E

N-{[4-({(1R)-3-(dimethylamino)-1-[(phenylthio)methyl]propyl}amino)-3-nitrophenyl]sulfonyl}-4-[4-(3-morpholin-4-yl-3-oxopropyl)phenyl]piperazine-1-carboxamide The desired product was prepared by substituting Example 4D for 1-phenylpiperazine in Example 1. MS (ESI) m/e 754 (M+H)$^+$; $^1$H NMR (500 MHz, DMSO-d$_6$) δ 8.50–6.50 (12H, m), 4.15 (1H, br), 3.60–3.28 (12H, m), 3.17 (2H, s), 3.06 (2H, m), 2.95 (2H, t), 2.65 (6H, s), 2.54 (2H, t), 2.17 (2H, m).

EXAMPLE 5

N-{[4-({(1R)-3-(dimethylamino)-1-[(phenylthio)methyl]propyl}amino)-3-nitrophenyl]sulfonyl}-4-[4-(3-morpholin-4-ylpropyl)phenyl]piperazine-1-carboxamide

EXAMPLE 5A

4-[3-(4-bromophenyl)propyl]morpholine

A solution of Example 4B (760 mg, 2.550 mmol) in THF (10 mL) at room temperature was treated with 5M BH$_3$/dimethylsulfide in diethyl ether (2.55 mL, 12.752 mmol), stirred for 24 hours, treated with 3N aqueous HCl (10 mL), heated to reflux for 1 hour, and partitioned between ethyl acetate and 1N NaOH. The aqueous layer was extracted with ethyl acetate (3×50 mL) and the combined extracts were dried (MgSO$_4$), filtered, and concentrated. The concentrate was purified by flash column chromatography on silica gel with 5% 2N NH$_3$ in methanol/dichloromethane to provide the desired product (565 mg, 78%).

EXAMPLE 5B tert-butyl 4-[4-(3-morpholin-4-ylpropyl)phenyl]piperazine-1-carboxylate The desired product was prepared by substituting Example 5A for Example 4B in Example 4C. $^1$H NMR (300 MHz, CDCl$_3$) δ 7.09 (2H, d), 6.85 (2H, d), 3.73 (4H, br), 3.57 (4H, t), 3.08 (4H, t), 2.58 (2H, t), 2.44 (6H, br), 1.75 (2H, br), 1.48 (9H, s).

EXAMPLE 5C

4-[3-(4-piperazin-1-ylphenyl)propyl]morpholine tris(trifluoroacetate)

A solution of Example 5B (671 mg, 1.725 mmol) in dichloromethane (2 mL) at room temperature was treated with TFA (1.8 mL) and water (0.2 mL) allowed to stand for 2 hours The solution was concentrated to provide the desired product.

EXAMPLE 5D

N-{[4-({(1R)-3-(dimethylamino)-1-[(phenylthio) methyl]propyl}amino)-3-nitrophenyl]sulfonyl}-4-[4-(3-morpholin-4-ylpropyl)phenyl]piperazine-1-carboxamide A suspension of 4-({(1R)-3-(dimethylamino)-1-[(phenylthio)methyl]propyl}amino)-3-nitrobenzenesulfonamide (prepared according to the procedure described in commonly owned U.S. patent application Ser. No. 09/957,256, filed Sep. 20, 2001, 20 mg, 0.0434 mmol) in THF (1.5 mL) at 0° C. was treated with NaH (8.6 mg, 0.217 mmol), warmed to room temperature, stirred for 1 hour, cooled to −20° C., treated with 1,1'-carbonyldiimidazolide (7.7 mg, 0.0477 mmol), slowly warmed to room temperature over 2 hours, quenched with acetic acid (25 µL, 0.434 mmol), treated with Example 5C (30 mg, 0.0477 mmol) and triethylamine (60 µL, 0.434 mmol), stirred for 5 hours, and concentrated. The concentrate was purified by flash column chromatography on silica gel with 20% 2N $NH_3$ in methanol/dichloromethane to provide the desired product (30 mg, 94%). MS (ESI) m/e 740 $(M+H)^+$; $^1H$ NMR (500 MHz, DMSO-$d_6$) δ 8.50–6.75 (12H, m), 4.15 (1H, m), 3.74 (4H, br s), 3.45 (4H, br s), 3.30 (4H, br), 3.13 (2H, m), 2.99 (4H, br s), 2.83 (2H, m), 2.73 (6H, s), 2.15 (2H, m), 1.85 (2H, m).

EXAMPLE 6

N-{[4-({(1R)-5-(dimethylamino)-1-[(phenylthio) methyl]pentyl}amino)-3-nitrophenyl]sulfonyl}-4-(4-fluorophenyl)-3,6-dihydropyridine-1(2H)-carboxamide

EXAMPLE 6A tert-butyl 4-[(trifluoroacetyl)oxy]-3,6-dihydropyridine-1(2H)-carboxylate A −78° C. solution of diisopropylamine (4 mL, 28.5 mmol) in THF (10 mL) was treated with 2.5M n-butyllithium in hexanes (10 mL), stirred for 1 hour, treated dropwise with a solution of tert-butyl 4-oxopiperidine-1-carboxylate (4.67 g, 23.4 mmol) in THF (20 mL), stirred for 1 hour, treated with a solution of 2-[N,N-bis(trifluoromethylsulfonyl)amino]pyridine (8.4 g, 23.4 mmol) in THF (20 mL), and warmed to room temperature overnight. The mixture was quenched with aqueous $NH_4Cl$ (50 mL), and extracted with ethyl acetate (3×50 mL). The combined extracts were washed with 1N NaOH (50 mL), dried ($Na_2CO_3$), filtered, and concentrated. The concentrate was loaded on a pad of $Al_2O_3$ (neutral, 100 g) and eluted with 1:9 ethyl acetate/hexanes to provide the desired product (5.73 g, 74%). MS (CI) m/e 332 $(M+H)^+$, 349 $(M+18)^+$.

EXAMPLE 6B tert-butyl 4-(4-fluorophenyl)-3,6-dihydropyridine-1(2H)-carboxylate A solution of Example 6A (4.0 g, 12 mmol) and 4-fluorophenylboronic acid (1.68 g, 12 mmol) in 1,2-dimethoxyethane (100 mL) and methanol (50 mL) was treated with tetrakis(triphenylphosphine)palladium(0) (0.416 g, 0.36 mmol) and CsF (3.64 g, 24 mmol), heated to reflux, and stirred overnight. The reaction was concentrated and the concentrate was dissolved in ethyl acetate (100 mL) and water (50 mL). The aqueous layer was extracted with ethyl acetate (2×50 mL) and the combined extracts were washed with water and brine, dried ($Na_2SO_4$), filtered, and concentrated. The concentrate was purified by flash column chromatography on silica gel with 1:6 ethyl acetate/hexanes to provide the desired product (2.6 g, 78%). MS(CI) m/e 278 $(M+H)^+$.

EXAMPLE 6C 4-(4-fluorophenyl)-1,2,3,6-tetrahydropyridine

A solution of Example 6B (0.5 g, 1.8 mmol) in dichloromethane (5 mL) at room temperature was treated with 2M HCl in diethyl ether (5 mL), stirred overnight, and concentrated to provide the desired product (0.45 g, 95%). MS (ESI) m/e 178 $(M+H)^+$.

EXAMPLE 6D

N-{[4-({(1R)-5-(dimethylamino)-1-[(phenylthio) methyl]pentyl}amino)-3-nitrophenyl]sulfonyl}-4-(4-fluorophenyl)-3,6-dihydropyridine-1(2H)-carboxamide The desired product was prepared by substituting Example 6C and 4-({(1R)-5-(dimethylamino)-1-[(phenylthio)methyl]pentyl}amino)-3-nitrobenzenesulfonamide (prepared according to the procedure described in commonly owned U.S. patent application Ser. No. 09/957,256, filed Sep. 20, 2001) for 1-(4-nitrophenyl)-piperazine and 4-({(1R)-3-(dimethylamino)-1-[(phenylthio)methyl] propyl}amino)-3-nitrobenzenesulfonamide, respectively, in Example 2. MS (ESI) m/e 656.2 $(M+H)^+$, 654.2 $(M-H)^-$; $^1H$ NMR (300 MHz, DMSO-$d_6$) δ 10.98 (s, 1H), 9.65 (m, 1H), 8.49(d, 1H), 8.30 (d, 1H), 7.84 (dd, 1H), 7.43–7.48 (m, 4H), 7.13–7.29 (m, 7H), 6.11 (m, 1H), 4.09 (m, 1H), 4.00 (m, 2H), 3.54 (m, 2H), 2.93–2.95 (m, 2H), 2.71 (s, 3H), 2.69 (s, 3H), 2.66 (m, 2H), 2.46 (m, 2H), 1.75 (m, 2H), 1.61 (m, 2H), 1.36 (m, 2H).

EXAMPLE 7

N-{[4-({(1R)-5-(dimethylamino)-1-[(phenylthio) methyl]pentyl}amino)-3-nitrophenyl]sulfonyl}-4-(4-fluorophenyl)piperidine-1-carboxamide

EXAMPLE 7A tert-butyl 4-(4-fluorophenyl)piperidine-1-carboxylate

A solution of Example 6B (2 g, 7.2 mmol) in ethanol (30 mL) was treated with 10% Pd/C (200 mg) and shaken at room temperature under 60 psi of $H_2$ for 4 hours. The mixture was filtered and the filter cake was washed with ethanol. The filtrate was concentrated to provide the desired product (1.95 g, 96%). MS (CI) m/e 280 (M+H)+.

EXAMPLE 7B 4-(4-fluorophenyl)piperidine

The desired product was prepared by substituting Example 7A for Example 6B in Example 6C. MS (ESI) m/e 180 (M+H)+.

EXAMPLE 7C

N-{[4-({(1R)-5-(dimethylamino)-1-[(phenylthio) methyl]pentyl}amino)-3-nitrophenyl]sulfonyl}-4-(4-fluorophenyl)piperidine-1-carboxamide The desired product was prepared by substituting Example 7B and 4-({(1R)-5-(dimethylamino)-1-[(phenylthio)methyl]pentyl}amino)-3-nitrobenzenesulfonamide (prepared according to the procedure described in commonly owned U.S. patent application Ser. No. 09/957,256, filed Sep. 20, 2001) for 1-(4-nitrophenyl)-piperazine and 4-({(1R)-3-(dimethylamino)-1-[(phenylthio)methyl]propyl}amino)-3-nitrobenzenesulfonamide, respectively, in Example 2. MS (ESI) m/e 658.2 (M+H)+, 656.2 (M−H)−; $^1$H NMR (300 MHz, DMSO-$d_6$) δ 10.98 (s, 1H), 9.60 (m, 1H), 8.49 (d, 1H), 8.30 (d, 1H), 7.83 (dd, 1H), 7.06–7.29 (m, 9H), 4.15 (m, 1H), 4.06 (m, 2H), 4.01 (m, 2H), 3.37 (m, 2H), 2.93–2.95 (m, 2H), 2.83 (m, 3H), 2.72 (s, 3H), 2.70 (s, 3H), 2.66 (m, 2H), 1.75 (m, 2H), 1.61 (m, 2H), 1.36 (m, 2H).

EXAMPLE 8

N-{[4-({(1R)-5-(dimethylamino)-1-[(phenylthio) methyl]pentyl}amino)-3-nitrophenyl]sulfonyl}-4-(4,4-dimethylcyclohexyl)piperazine-1-carboxamide

EXAMPLE 8A 4,4-dimethylcyclohexanone

A solution of 4,4-dimethyl-2-cyclohexen-1-one (25.37 g, 0.204 mol) in ethanol at room temperature (200 mL) was treated with 10% Pd/C catalyst (1.5 g) and agitated under 60 psi $H_2$ for 4 hours. The reaction was filtered and the filter cake was washed with ethanol. The filtrate was concentrated to provide the desired product (22.4 g, 87%). MS (CI) m/e 127 (M+H)+.

EXAMPLE 8B tert-butyl 4-(4,4-dimethylcyclohexyl)piperazine-1-carboxylate

A solution of Example 8A (0.28 g, 2.2 mmol) and 1-tert-butoxycarbonylpiperazine (0.42 g, 2.2 mmol) in dichloroethane (5 mL) at room temperature was treated with acetic acid (100 μL) and sodium triacetoxyborohydride (0.53 g, 2.5 mmol), stirred overnight, diluted with ethyl acetate (300 mL), washed sequentially with 1N NaOH, water, and brine, dried ($Na_2SO_4$), filtered, and concentrated to provide the desired product (650 mg, 95%). MS (ESI) m/e 297 (M+H)+.

EXAMPLE 8C 1-(4,4-dimethylcyclohexyl)piperazine

The desired product was prepared by substituting Example 8B for Example 6B in Example 6C. MS (ESI) m/e 197 (M+H)+.

EXAMPLE 8D

N-{[4-({(1R)-5-(dimethylamino)-1-[(phenylthio) methyl]pentyl}amino)-3-nitrophenyl]sulfonyl}-4-(4,4-dimethylcyclohexyl)piperazine-1-carboxamide The desired product was prepared by substituting Example 8C and 4-({(1R)-5-(dimethylamino)-1-[(phenylthio)methyl]pentyl}amino)-3-nitrobenzenesulfonamide (prepared according to the procedure described in commonly owned U.S. patent application Ser. No. 09/957,256, filed Sep. 20, 2001) for 1-(4-nitrophenyl)-piperazine and 4-({(1R)-3-(dimethylamino)-1-[(phenylthio)methyl]propyl}amino)-3-nitrobenzenesulfonamide, respectively, in Example 2. MS (ESI) m/e 675.3 (M+H)+, 673.3 (M−H)−; $^1$H NMR (300 MHz, DMSO-$d_6$) δ 10.56 (s, 1H), 9.81 (m, 1H), 8.49 (d, 1H), 8.31 (d, 1H), 7.82 (dd, 1H), 7.15–7.30 (m, 5H), 4.13 (m, 1H), 4.07 (m, 2H), 4.02 (m, 2H), 3.07 (m, 2H), 2.95 (m, 4H), 2.71 (s, 3H), 2.69 (s, 3H), 2.66 (m, 2H), 1.86–1.90 (m, 2H), 1.77 (m, 2H), 1.61 (m, 4H), 1.11–1.49 (m, 4H), 0.89 (s, 6H).

EXAMPLE 9

N-55 [4-({(1R)-3-(dimethylamino)-1-[(phenylthio) methyl]propyl}amino)-3-nitrophenyl]sulfonyl}-4-(4,4-dimethylcyclohexyl)piperazine-1-carboxamide The desired product was prepared by substituting Example 8C for 1-(4-nitrophenyl)-piperazine in Example 2. MS (ESI) m/e 647.3 (M+H)+, 645.3 (M−H)−; $^1$H NMR (300 MHz, DMSO-$d_6$) δ 10.90 (s, 1H), 10.32 (m, 1H), 8.49 (d, 1H), 8.30 (d, 1H), 7.81 (dd, 1H), 7.18–7.29 (m, 5H), 4.25 (m, 1H), 4.04 (m, 1H), 3.88 (m, 4H), 3.46–3.52 (m, 2H), 3.40 (m, 2H), 2.95–3.1 (m, 2H), 2.71 (m, 6H), 2.18 (m, 2H), 1.82 (m, 2H), 1.61 (m, 2H), 1.43 (m, 2H), 1.16–1.22 (m, 2H), 0.89 (s, 6H).

EXAMPLE 10

N-{[4-({(1R)-5-(dimethylamino)-1-[(phenylthio) methyl]pentyl}amino)-3-nitrophenyl]sulfonyl}-4,4'-dimethyl-1,4'-bipiperidine-1'-carboxamide

Example 10A 4,4-dimethylpiperidine

A suspension of $LiAlH_4$ (5.5 g, 145 mmol) in diethyl ether (300 mL) was treated in portions with 3,3-dimethylglutarimide (8.5 g, 57.7 mmol), heated to reflux, stirred overnight, cooled to room temperature, and treated with 1N NaOH (70 mL). The solution was decanted and the remaining solid was washed with diethyl ether (3×200 mL). The combined organic washes were washed with brine, dried ($Na_2SO_4$), filtered, and concentrated to a volume of 200 mL. The solution was treated with 2M HCl in diethyl ether (50 mL) and the mixture was filtered and the filter cake was washed with diethyl ether (3×150 mL) to provide the desired product (6.58 g, 76%). MS (CI) m/e 114 (M+H)⁺.

EXAMPLE 10B tert-butyl 4,4-dimethyl-1,4'-bipiperidine-1'-carboxylate

The desired product was prepared by substituting Example 10A and tert-butyl 4-oxo-1-piperidinecarboxylate for Example 8A and 1-tert-butoxycarbonylpiperazine, respectively, in Example 8B. MS (CI) m/e 297 (M+H)⁺.

EXAMPLE 10C 4,4-dimethyl-1,4'-bipiperidine

The desired compound was prepared by substituting Example 10B for Example 6B in Example 6C. MS (ESI) m/e 197 (M+H)⁺.

EXAMPLE 10D

N-{[4-({(1R)-5-(dimethylamino)-1-[(phenylthio)methyl]pentyl}amino)-3-nitrophenyl]sulfonyl}-4,4-dimethyl-1,4'-bipiperidine-1'-carboxamide The desired product was prepared by substituting Example 10C and 4-({(1R)-5-(dimethylamino)-1-[(phenylthio)methyl]pentyl}amino)-3-nitrobenzenesulfonamide (prepared according to the procedure described in commonly owned U.S. patent application Ser. No. 09/957,256, filed Sep. 20, 2001) for 1-(4-nitrophenyl)-piperazine and 4-({(1R)-3-(dimethylamino)-1-[(phenylthio)methyl]propyl}amino)-3-nitrobenzenesulfonamide, respectively, in Example 2. MS (ESI) m/e 675.4 (M+H)⁺, 673.3 (M−H)⁻; ¹H NMR (300 MHz, DMSO-d₆) δ 11.02 (s, 1H), 9.95 (m, 1H), 8.48 (d, 1H), 8.31 (d, 1H), 7.81 (dd, 1H), 7.13–7.29 (m, 5H), 4.02–4.15 (m, 2H), 3.29 (m, 4H), 2.97 (m, 4H), 2.75 (m, 2H), 2.71 (s, 3H), 2.69 (s, 3H), 2.10 (m, 2H), 1.75 (m, 4H), 1.62 (m, 4H), 1.52 (m, 4H), 1.37 (m, 2H), 0.97 (s, 6H).

EXAMPLE 11

4-(4-benzyl-4-methoxycyclohexyl)-N-{[4-({(1R)-3-(dimethylamino)-1-[(phenylthio)methyl]propyl}amino)-3-nitrophenyl]sulfonyl}piperazine-1-carboxamide

EXAMPLE 11A 8-benzyl-1,4-dioxaspiro[4.5]decan-8-ol

A 0° C. solution of 2M benzylmagnesium chloride in THF (20 mL) was treated with a solution of 1,4-cyclohexanedione mono-ethylene ketal (6.24 g, 40 mmol) in THF (50 mL), warmed to room temperature, stirred overnight, quenched with saturated NH₄Cl (100 mL), and extracted with ethyl acetate (3×100 mL). The combined extracts were washed with water and brine, dried (Na₂SO₄), filtered, and concentrated. The concentrate was purified by flash column chromatography on silica gel with 6:1 hexanes/ethyl acetate to provide the desired product (8.08 g, 81%). MS (CI) m/e 231(M−18)⁺, 249 (M+H) ⁺, 266.2 (M+18)⁺.

EXAMPLE 11B 8-benzyl-8-methoxy-1,4-dioxaspiro[4.5]decane

A solution of Example 11A (8.08 g, 32.5 mmol) in THF (150 mL) at room temperature was treated with 60% NaH in mineral oil (3.2 g, 80 mmol), stirred for 1 hour, treated with iodomethane (5 mL, 80 mmol), stirred overnight, quenched with saturated NH₄Cl, and extracted with ethyl acetate (3×200 mL). The combined extracts were washed with water and brine, dried (Na₂SO₄), filtered, and concentrated to provide the desired product. MS (CI) m/e 280.2 (M+18)⁺.

EXAMPLE 11C 4-benzyl-4-methoxycyclohexanone

A solution of Example 11B (8.5 g, 32.5 mmol) in acetone (200 mL) was treated with water (100 mL) and p-toluenesulfonic acid monohydrate (1 g), heated to reflux, stirred overnight, and concentrated to remove the acetone. The remaining aqueous solution was extracted with ethyl acetate (3×1 00 mL) and the combined extracts were washed sequentially with 1N NaOH, water, and brine, dried (Na₂SO₄), filtered, and concentrated to provide the desired product (6.95 g, 95%). MS (CI) m/e 236.2 (M+18)⁺.

EXAMPLE 11D tert-butyl 4-(4-benzyl-4-methoxycyclohexyl)piperazine-1-carboxylate The desired product was prepared by substituting Example 11C for Example 8A in Example 8B. MS (ESI) m/e 389.2 (M+H)⁺.

EXAMPLE 11E 1-(4-benzyl-4-methoxycyclohexyl)piperazine

The desired product was prepared by substituting Example 11D for Example 6B in Example 6C. MS (ESI) m/e 289.2 (M+H)⁺.

EXAMPLE 11F 4-(4-benzyl-4-methoxycyclohexyl)-N-{[4-({(1R)-3-(dimethylamino)-1-[(phenylthio)methyl]propyl}amino)-3-nitrophenyl]sulfonyl}piperazine-1-carboxamide The desired product was prepared by substituting Example 11E for 1-(4-nitrophenyl)-piperazine in Example 2. MS (ESI) m/e 739.4 (M+H)⁺, 737.4 (M−H)⁻; ¹H NMR (300 MHz, DMSO-d₆) δ 10.52 (s, 1H), 10.20 (m, 1H), 8.49 (d, 1H), 8.29 (d, 1H), 7.80 (dd, 1H), 7.13–7.29 (m, 10H), 4.24 (m, 1H), 4.00–4.05 (m, 2H), 3.40 (m, 4H), 3.22 (s, 3H), 3.14 (m, 4H), 2.92 (m, 2H), 2.71 (s, 6H), 2.16 (m, 2H), 1.81 (m, 4H), 1.75 (m, 4H), 1.51 (m, 2H), 1.36 (m, 2H),

EXAMPLE 12

N-{[4-({(1R)-3-(dimethylamino)-1-[(phenylthio)
methyl]propyl}amino)-3-nitrophenyl]sulfonyl}-4-(4,
4-dimethylcyclohexyl)piperidine-1-carboxamide

EXAMPLE 12A 4,4-dimethylcyclohex-1-en-1-yl trifluoroacetate

The desired compound was prepared by substituting Example 8A for tert-butyl 4-oxopiperidine-1-carboxylate in Example 6A. MS(CI) m/e 258 (M+H)$^+$.

EXAMPLE 12B 4-(4,4-dimethylcyclohex-1-en-1-yl)pyridine

A solution of Example 12A (0.775 g. 3.0 mmol) and 4-tributylstannylpyridine(1.22 g, 3.3 mmol) in 1-methyl-2-pyrrolidinone (5 mL) was treated with Pd$_2$(dba)$_3$ (55 mg, 0.06 mmol), CuI (65 mg, 0.35 mmol), Ph$_3$P (125 mg, 0,475 mmol) and K$_2$CO$_3$ (550 mg, 3.9 mmol), purged with argon, and stirred for 25 hours at 90° C. The reaction mixture was diluted with ethyl acetate (50 mL) and saturated aqueous potassium fluoride (10 mL), stirred 2 hoursr at room temperature, and filtered through a pad of diatomaceous earth (Celite®). The filtrate layers were separated and the organic phase was washed with water and brine, dried (Na$_2$SO$_4$), filtered, and concentrated. The concentrate was purified by flash column chromatography on silica gel with 4:1 ethyl acetate and hexanes to provide 200 mg (36%) of the desired product. MS(ESI) m/e 188.1 (M+H)$^+$.

EXAMPLE 12C 4-(4,4-dimethylcyclohexyl)piperidine Hydrochloride

A solution of Example 12B (200 mg, 1.07 mmol) in acetic acid (10 mL) was treated with PtO$_2$ (80 mg) and stirred under 4 atm of H$_2$ at room temperature for 72 hours. The mixtre was filtered and the filtrate was concentrated. The concentrate was dissolved in dichloromethane (5 mL) and 2M HCl in diethyl ether (5 mL) and concentrated to provide 150 mg (72%) of the desired product. MS(ESI) m/e 196.1 (M+H)$^+$.

EXAMPLE 12D

N-{[4-({(1R)-3-(dimethylamino)-1-[(phenylthio)
methyl]propyl}amino)-3-nitrophenyl]sulfonyl}-4-(4,
4-dimethylcyclohexyl)piperidine-1-carboxamide The desired product was prepared by substituting Example 12C for 1-(4-nitrophenyl)-piperazine in Example 2. MS (ESI) m/e 646.3 (M+H)$^+$, 644.3 (M–H)$^-$; $^1$H NMR (300 MHz, DMSO-d$_6$) δ 10.80 (s, 1H), 9.87 (m, 1H), 8.47 (d, 1H), 8.27 (d, 1H), 7.80 (dd, 1H), 7.14–7.27 (m, 5H), 4.22 (m, 1H), 3.93 (m, 2H), 3.76 (m, 4H), 3.14 (m, 2H), 2.73 (m, 4H), 2.65 (m, 2H), 2.17 (m, 2H), 1.66 (m, 2H), 1.46 (m, 2H), 1.32 (m, 2H), 1.09 (m 8H), 0.857 (s, 3H), 0.822 (s, 3H).

EXAMPLE 13

4-{4-[acetyl(benzyl)amino]phenyl}-N-{[4-({(1R)-3-
(dimethylamino)-1-[(phenylthio)methyl]
propyl}amino)-3-nitrophenyl]sulfonyl}-3,6-dihydro-
pyridine-1(2H)-carboxamide

EXAMPLE 13A tert-butyl 4-(trimethylstannyl)-3,6-dihydropyridine-1
(2H)-carboxylate A solution of Example 6A (5.62 g, 16.95 mmol) in dioxane (80 mL) was treated with hexamethyldistannane (5.0 g, 15.26 mmol), lithium chloride (4.07 g, 96.0 mmol), and tetrakis(tirphenylphosphine)palladium (0) (0.333 g, 0.288 mmol) and was stirred at reflux overnight. The mixture was cooled to room temperature, concentrated, dissolved in dichloromethane (200 mL), treated with saturated aqueous KF (200 mL), stirred at room temperature for 1 hour, and filtered through diatomaceous earth (Celite®). The filtrate layers were separated and the organic phase washed with water and brine, dried (Na$_2$SO$_4$), filtered, and concentrated. The concentrate was purified by flash column chromatography on silica gel with 10:1 hexanes/ethyl acetate to provide 4.6 g (83%) of the desired product. MS(CI): m/e 348 (M+H)$^+$.

EXAMPLE 13B

N-benzyl-N-(4-bromophenyl)amine

A solution of 4-bromoaniline (1.76 g, 10 mmol) and benzaldehyde (1.06 g, 10 mmol) in dichloroethane (15 mL) was treated with NaBH(OAc)$_3$ (2.32 g, 11 mmol) and glacial acetic acid (1 mL), stirred overnight at room temperature, quenched with 1N NaOH, and extracted with CH$_2$Cl$_2$ (3×50 mL). The combined extracts were washed with water and brine, dried, (Na$_2$SO$_4$), filtered, and concentrated. The concentrate was purified by flash column chromatography on silica gel with 5:1 hexanes/ethyl acetate to provide 2.21 g (84%) of the desired product. MS(ESI) m/e 261.9 (M+H)$^+$, 263.9 (M+H)$^+$.

EXAMPLE 13C

N-benzyl-N-(4-bromophenyl)acetamide

A solution of Example 14B (2.21 g, 8.4 mmol) in dichloromethane (50 mL) was treated with diisopropylethylamine (3 mL) and acetyl chloride (3 mL), stirred at room temperature for 30 minutes, diluted with dichloromethane (150 mL), washed sequentially with 6N HCl, water, 1N NaOH, water, and brine; dried (Na$_2$SO$_4$), filtered, and concentrated to provide 2.47 g (97%) of the desired product. MS(ESI) m/e 303.9 (M+H)$^+$, 305.9 (M+H)$^+$.

EXAMPLE 13D tert-butyl 4-{4-[acetyl(benzyl)amino]phenyl}-3,6-
dihydropyridine-1(2H)-carboxylate A solution of Example 14A (0.346 g, 1.0 mmol) and Example 14C (0.304 g, 1.0 mmol) in dioxane (1 5 mL) was treated with tetrakis(triphenylphosphine)palladium (0) (5 8 mg, 0.05 mmol) and cuprous bromide (10 mg, 0.07 mmol) and heated to reflux under nitrogen for 15 hours. The mixture was cooled to room temperature, concentrated, dissolved in ethyl acetate (100 mL), treated with saturated aqueous KF (10 mL) stirred at room temperature for 1 hour, and filtered through diatomaceous earth (Celite®). The filtrate layers were separated and the organic phase was washed with water and brine, dried ($Na_2SO_4$), filtered, and concentrated. The concentrate was purified by flash column chromatography on silica gel with 10:1 hexanes/ethyl acetate to provide 0.190 g (47%) of the desired product. MS(ESI) m/e 407.1 $(M+H)^+$.

EXAMPLE 13E

4-{4-[acetyl(benzyl)amino]phenyl}-N-{[4-({(1R)-3-(dimethylamino)-1-[(phenylthio)methyl]propyl}amino)-3-nitrophenyl]sulfonyl}-3,6-dihydro-pyridine-1(2H)-carboxamide A solution of Example 14D (0.095 g, 0.024 mmol) in dichloromethane (2 mL) was treated with 2M HCl in diethyl ether (4 mL), stirred at room temperature for 1 hour, and concentrated. The desired product was prepared by substituting this product for 1-(4-nitrophenyl)-piperazine in Example 2. MS (ESI) m/e 757.3 $(M+H)^+$, 755.3 $(M-H)^-$; $^1H$ NMR (300 MHz, DMSO-$d_6$) δ 10.98 (s, 1H), 9.85 (m, 1H), 8.51 (d, 1H), 8.28 (d, 1H), 7.84 (dd, 1H), 7.41 (d, 2H), 7.14–7.28 (m, 12H), 6.18 (m, 1H), 4.85 (s, 2H), 4.20 (m, 1H), 4.00 (m, 2H), 3.51(m, 2H), 3.14 (m, 2H), 2.73 (m, 6H), 2.45 (m, 2H), 2.15 (m, 2H), 1.82 (s, 3H).

EXAMPLE 14

4-{4-[acetyl(benzyl)amino]phenyl}-N-{[4-({(1R)-3-(dimethylamino)-1-[(phenylthio)methyl]propyl}amino)-3-nitrophenyl]sulfonyl}piperidine-1-carboxamide

EXAMPLE 14A tert-butyl 4-{4-[acetyl(benzyl)amino]phenyl}piperidine-1-carboxylate A solution of Example 14D (0.090 g, 0.22 mmol) in methanol (10 mL) was treated with 10% Pd/C (30 mg) and stirred under 1 atm hydrogen at room temperature for 2 hours, filtered, and concentrated. The concentrate was purified by flash column chromatography on silica gel with 2:1 hexanes/ethyl acetate to provide 0.075 g (83%) of the desired product. MS(ESI) m/e 409.2 $(M+H)^+$.

EXAMPLE 14B

4-{4-[acetyl(benzyl)amino]phenyl}-N-{[4-({(1R)-3-(dimethylamino)-1-[(phenylthio)methyl]propyl}amino)-3-nitrophenyl]sulfonyl}piperidine-1-carboxamide A solution of Example 15A in dichloromethane (2 mL) was treated with 2M HCl in diethyl ether (4 mL), stirred at room temperature, and concentrated. The desired product was prepared by substituting this product for 1-(4-nitrophenyl)-piperazine in Example 2. MS (ESI) m/e 759.4 $(M+H)^+$, 757.3 $(M-H)^-$; $^1H$ NMR (300 MHz, DMSO-$d_6$) δ 10.90 (s, 1H), 9.82 (m, 1H), 8.50 (d, 1H), 8.39 (d, 1H), 7.82 (dd, 1H), 7.08–7.29 (m, 14H), 4.82 (s, 2H), 4.21 (m, 1H), 4.01 (m, 2H), 3.14 (m, 2H), 2.73 (m, 6H), 2.19 (m, 2H), 1.82 (s, 3H), 1.77 (m, 2H), 1.42 (m, 2H).

EXAMPLE 15

N-{[4-({(1R)-3-(dimethylamino)-1-[(phenylthio)methyl]propyl}amino)-3-nitrophenyl]sulfonyl}-4-[2-methoxy-4-(3-morpholin-4-ylpropyl)phenyl]piperidine-1-carboxamide

EXAMPLE 15A 4-chloro-2-methoxyphenyl trifluoroacetate

A solution of 4-chloro-2-methoxyphenol (10.0 g, 63.0 mmol) in pyridine (30 mL) was cooled to 0° C., treated with trifluoromethanesulfonic anhydride (17.8 g, 63.0 mmol), stirred 30 minutes, warmed to room temperature, and stirred for 24 hours. The reaction mixture was poured into water and extracted with ether (3×150 mL). The combined extracts were washed sequentially with water, 10% HCl (2×), water, and brine; dried ($Na_2SO_4$), filtered, and concentrated to provide 19.0 g of the desired product. MS(CI) m/e 290.1 $(M)^+$.

EXAMPLE 15B tert-butyl 4-(4-chloro-2-methoxyphenyl)-3,6-dihydropyridine-1(2H)-carboxylate A solution of Example 16A (0.346 g, 1.00 mmol) and Example 14A (0.290 g, 1.00 mmol) in dioxane (4 mL) was treated with LiCl (0.127 g, 3.00 mmol) and $Pd(Ph_3P)_4$ (0.023 g, 0.020 mmol) and was heated to 105° C. overnight. The mixture was cooled to room temperature, concentrated, dissolved in ethyl acetate (100 mL), treated with saturated aqueous KF (10 mL), stirred at room temperature for 1 hour, and filtered throught diatomaceous earth (Celite®). The filtrate layers were separated and the organic phase was washed with water and brine, dried ($Na_2SO_4$), filtered, and concentrated. The concentrate was purified by flash column chromatography on silica gel with 6:1 hexanes/ethyl acetate to provide 0.227 g (70.0%) of the desired product. MS(CI) m/e 324.1 $(M)^+$.

EXAMPLE 15C tert-butyl 4-{2-methoxy-4-[(1E)-3-morpholin-4-yl-3-oxoprop-1-enyl]phenyl}-3,6-dihydropyridine-1(2H)-carboxylate A solution of Example 16B (0.057 g, 0.176 mmol) and 4-acryloylmorpholine (0.050 g, 0.352 mmol) in dioxane (1 mL) was treated with $Pd_2(dba)_3$ (2.42 mg, 0.0026 mmol), N-methyldicyclohexaylamine (0.069 g, 0.352 mmol), and $P(t-Bu)_3$ (0.0012 g, 0.0056 mmol) and stirred at 120° C. overnight. The mixture was cooled to room temperature, diluted with ethyl acetate (100 mL), washed with water and brine, dried ($Na_2SO_4$), filtered, and concentrated. The concentrate was purified by flash column chromatography on silica gel with 20:1 dichloromethane/methanol to provide 0.070 g (93%) of the desired product. MS(ESI) m/e 429.2 $(M+1)^+$.

EXAMPLE 15D tert-butyl 4-[2-methoxy-4-(3-morpholin-4-yl-3-oxopropyl)phenyl]piperidine-1-carboxylate The desired product was prepared by substituting Example 16C for Example 14D in Example 15A. The

EXAMPLE 15E tert-butyl 4-[2-methoxy-4-(3-morpholin-4-ylpropyl)phenyl]piperidine-1-carboxylate A solution of Example 16D (0.080 g, 0.185 mmol) in THF (2 mL) was treated with 2M $BH_3 \cdot Me_2S$ in THF (0.5 mL), stirred at room temperature for 3 hours, concentrated, dissolved in methanol (5 mL), stirred for 72 hours at room temperature, and concentrated. The concentrate was purified by flash column chromatography on silica gel with 20:1 dichloromethane/methanol to provide 0.070 g (90%) of the desired product. MS(ESI) m/e 419.2 $(M+1)^+$.

EXAMPLE 15F

N-{[4-({(1R)-3-(dimethylamino)-1-[(phenylthio)methyl]propyl}amino)-3-nitrophenyl]sulfonyl}-4-[2-methoxy-4-(3-morpholin-4-ylpropyl)phenyl]piperidine-1-carboxamide A solution of Example 16E in dichloromethane (2 mL) was treated with 2M HCl in diethyl ether (4 mL), stirred at room temperature for 1 hour, and concentrated. The desired product was prepared by substituting this product for 1-(4-nitrophenyl)-piperazine in Example 2. MS (ESI) m/e 769.4 $(M+H)^+$, 767.3 $(M-H)^-$; $^1H$ NMR (300 MHz, DMSO-$d_6$) δ 10.92 (s, 1H),10.52 (m, 1H), 10.02 (m, 1H), 8.50 (d, 1H), 8.29 (d, 1H), 7.84 (dd, 1H), 7.13–7.29 (m, 5H), 7.02 (d, 1H), 6.83 (d, 1H), 6.75 (dd, 1H), 4.23 (m, 1H), 4.02 (m, 2H), 3.95 (m, 2H), 3.78 (s, 3H), 3.75 (m, 2H), 3.40 (m, 2H), 3.14 (m, 2H), 2.73 (m, 6H), 2.60 (t, 2H), 2.19 (m, 2H), 2.00 (m, 2H), 1.70 (m, 2H), 1.45 (m, 2H).

Following the procedures described in the examples and the schemes, the following compounds may be prepared:

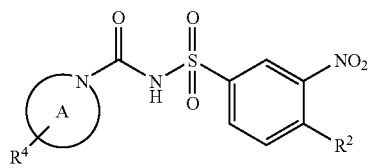

wherein $R^2$ is one of the following structures:

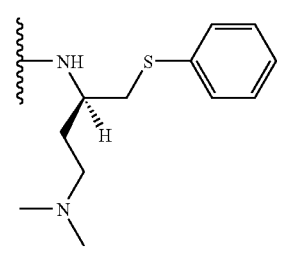

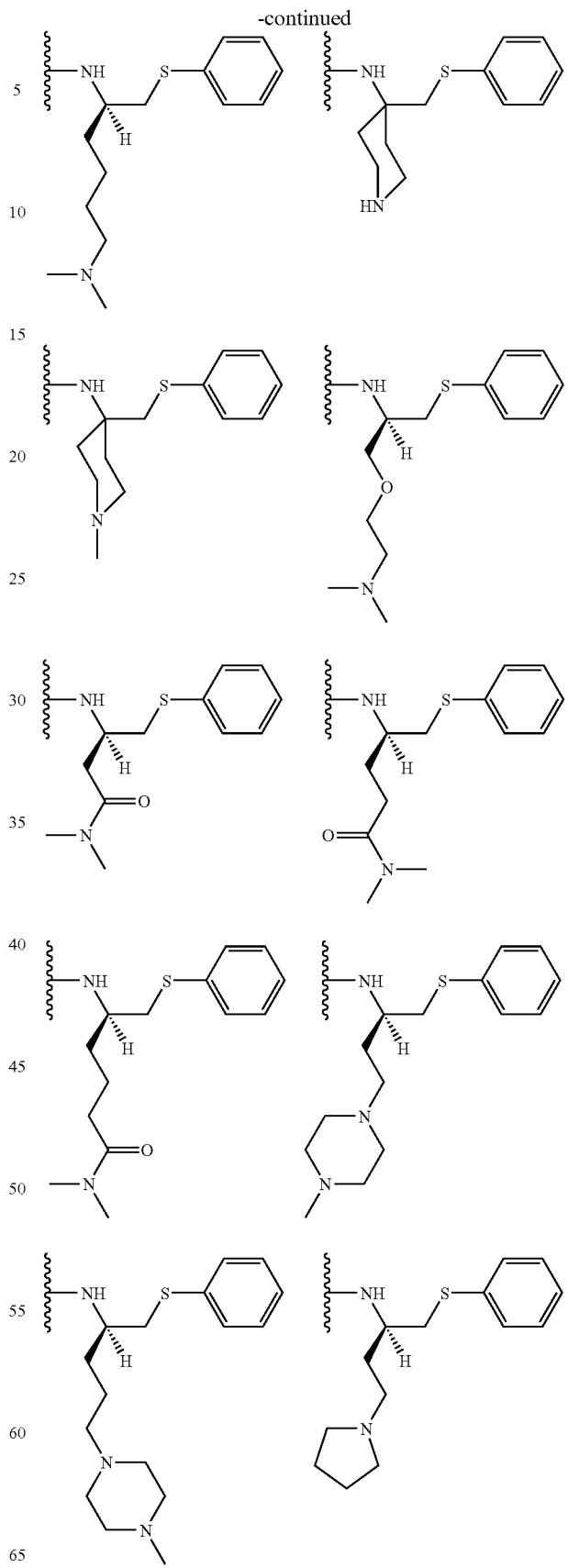

-continued
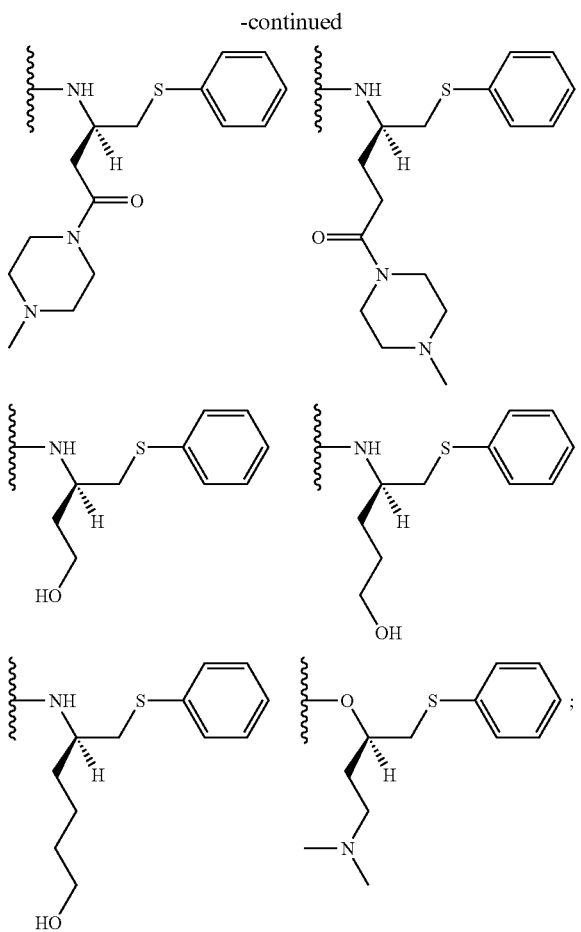
A is one of the following structures:
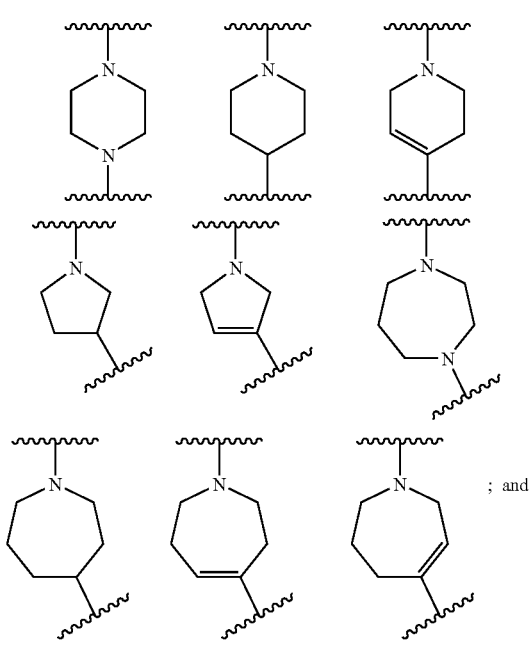
; and
R⁴ is one of the following structures:
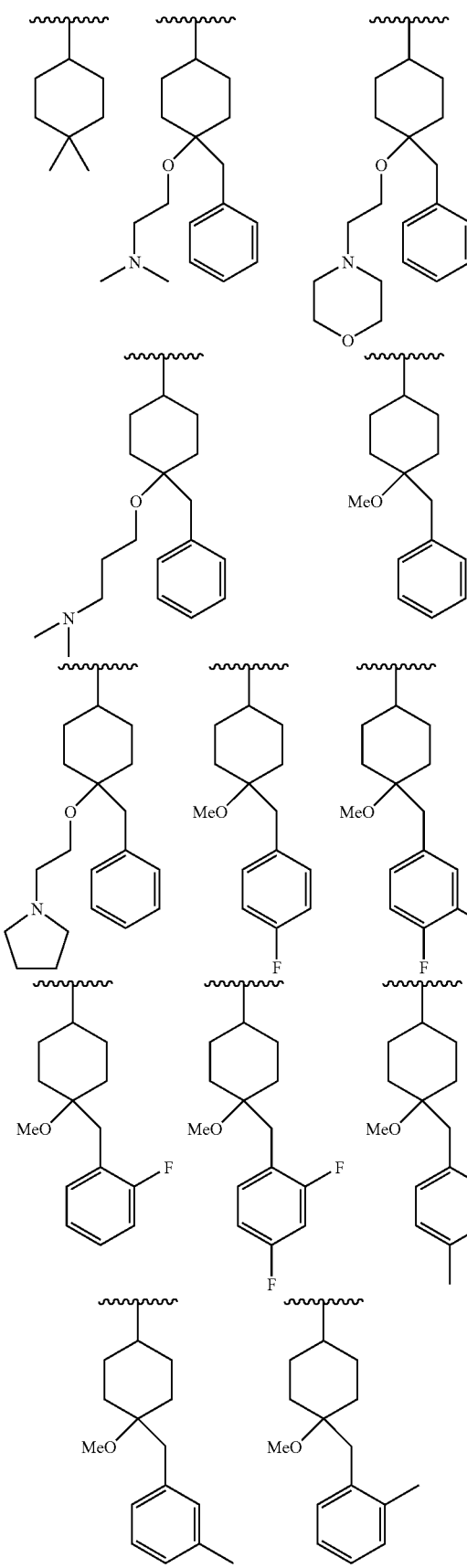

-continued
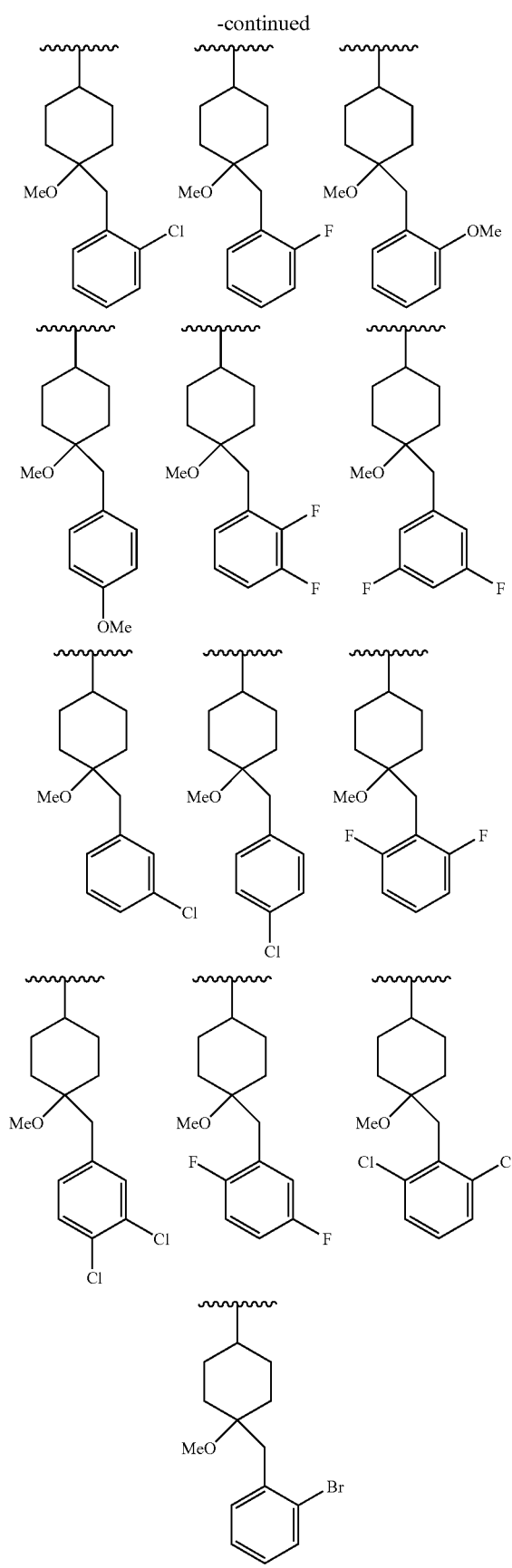
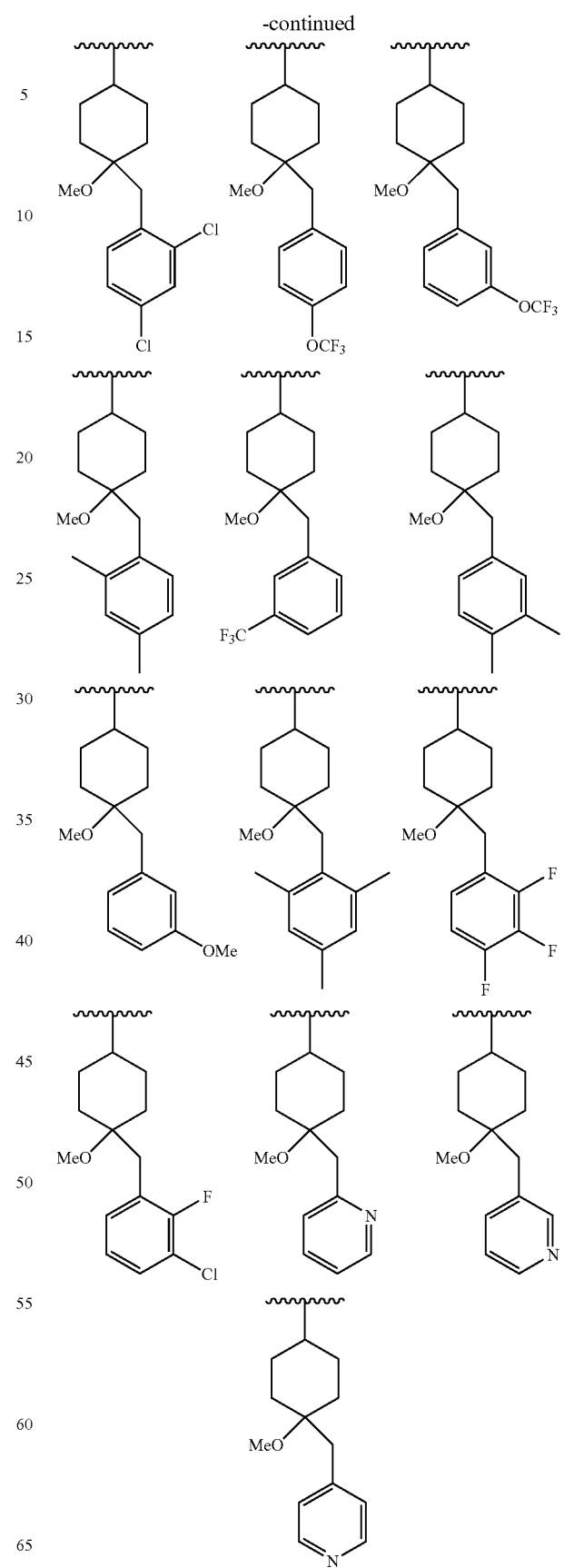

-continued
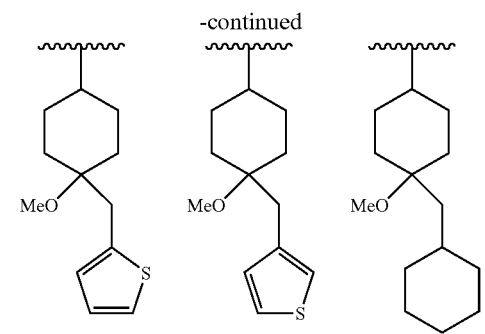
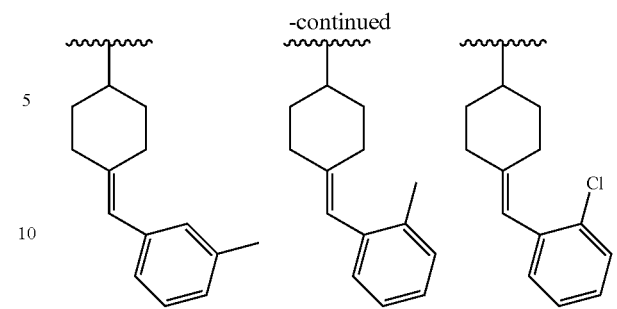
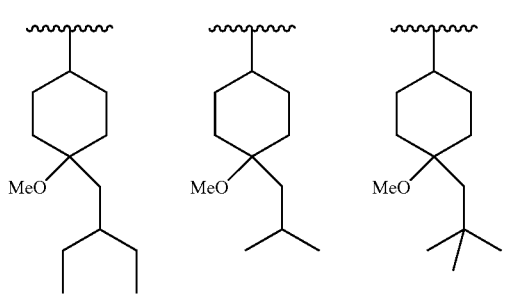
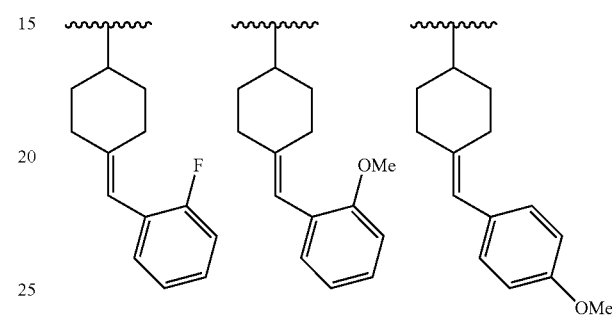
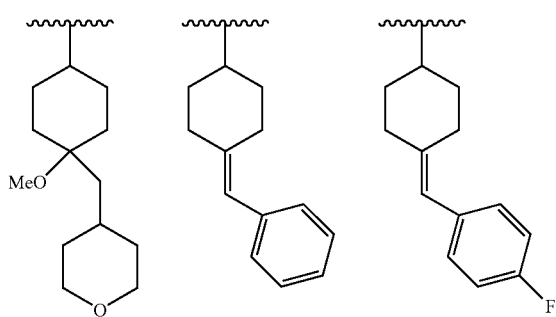
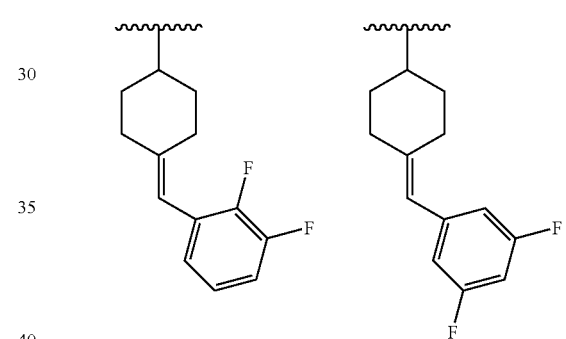
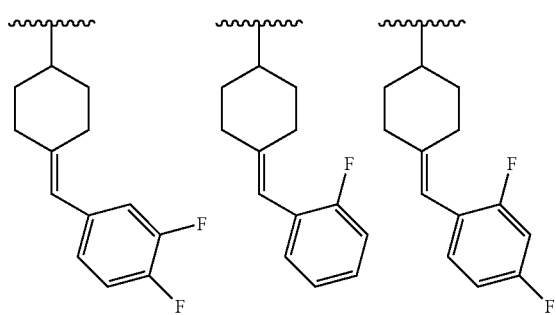
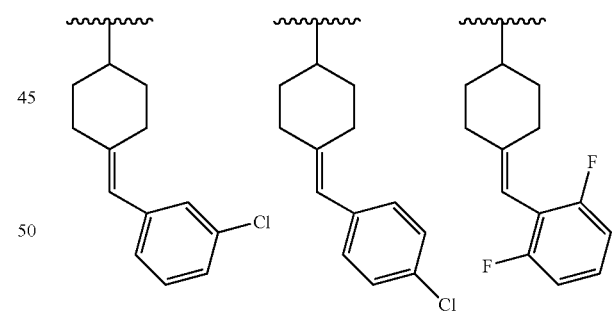
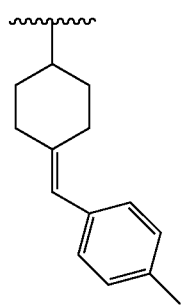
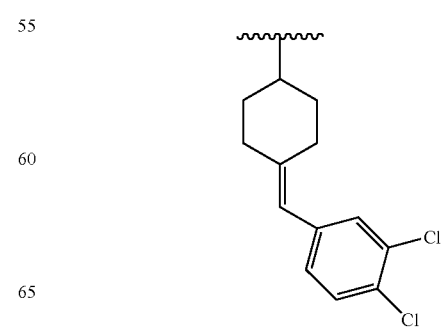

-continued
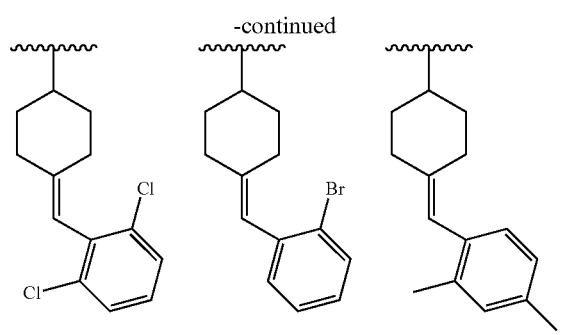
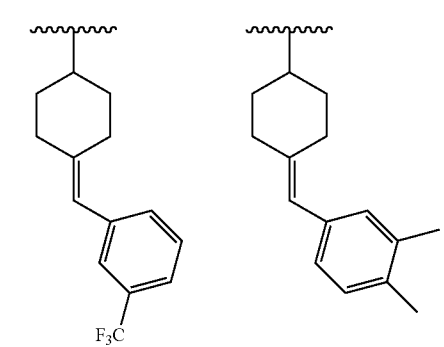
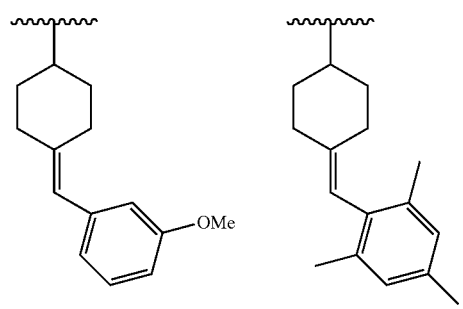
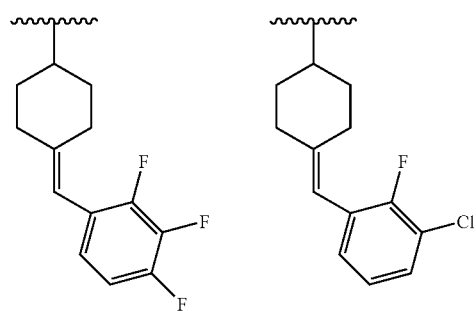
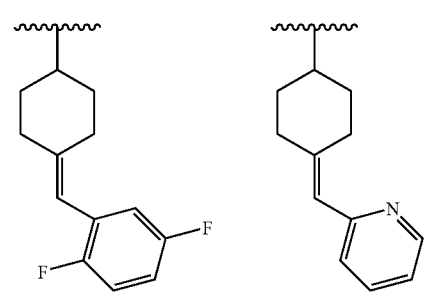
-continued
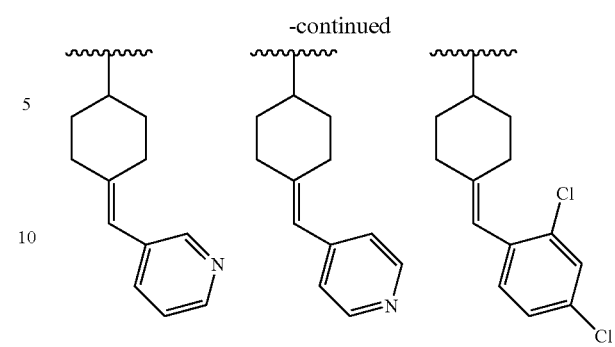
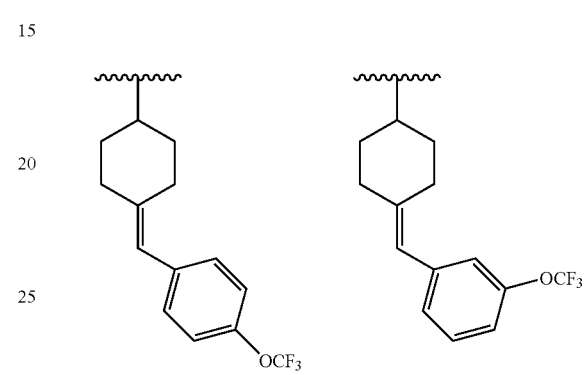
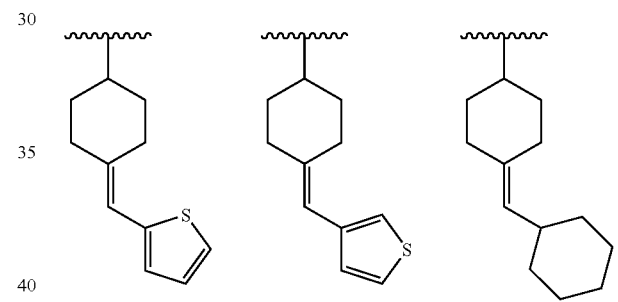
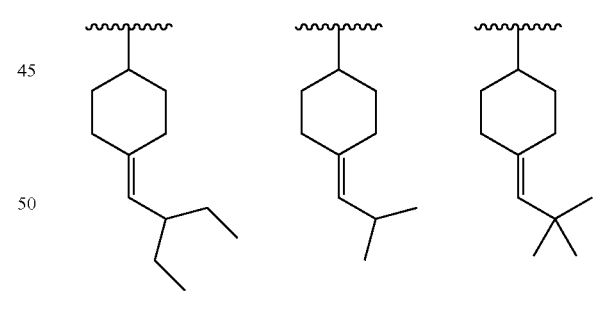
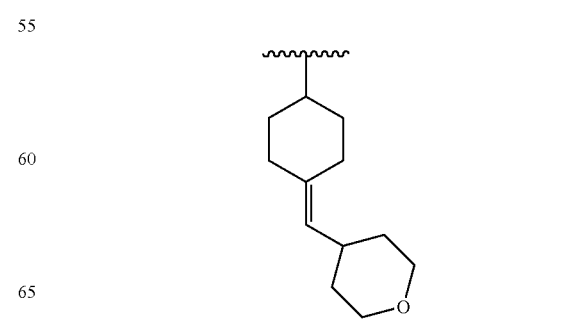

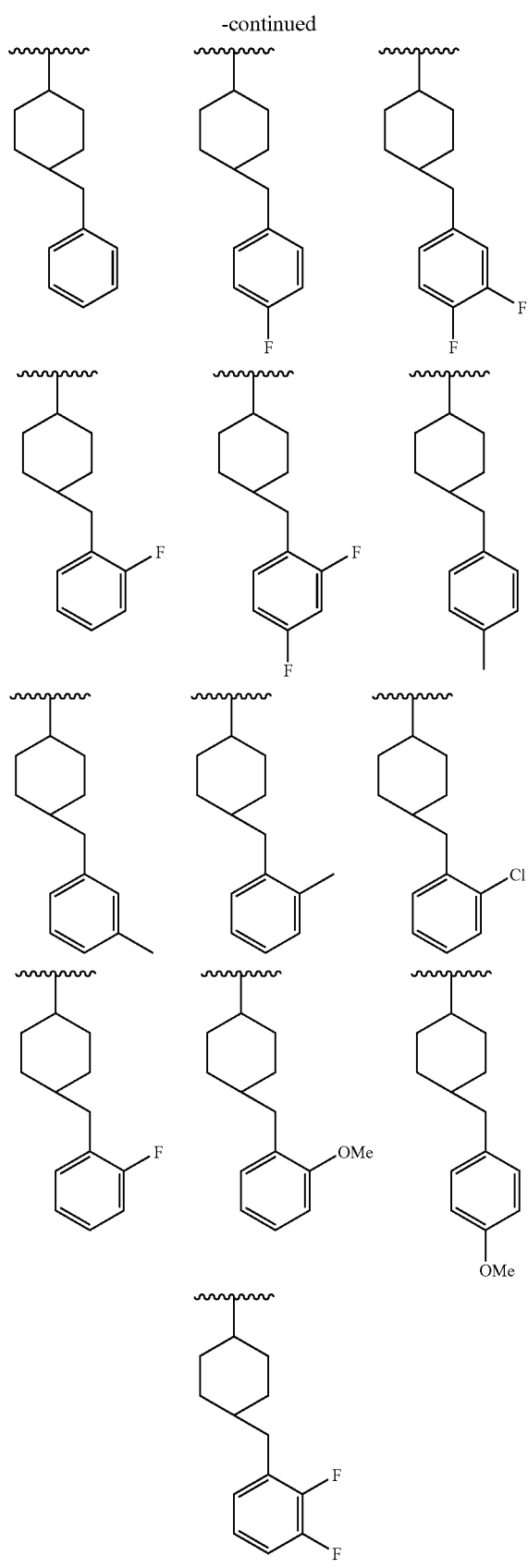
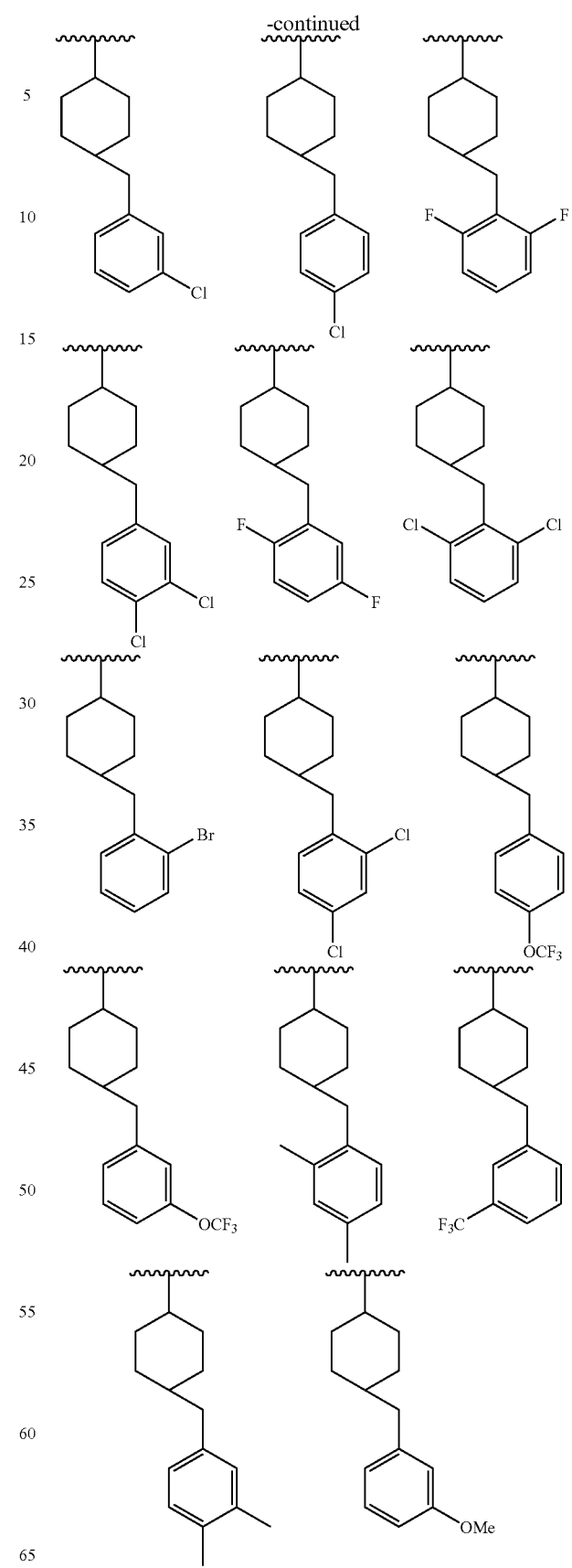

-continued
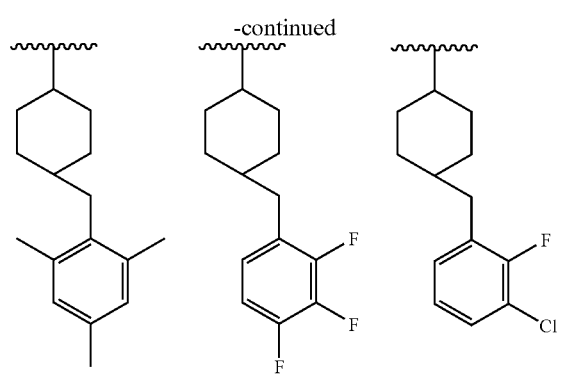
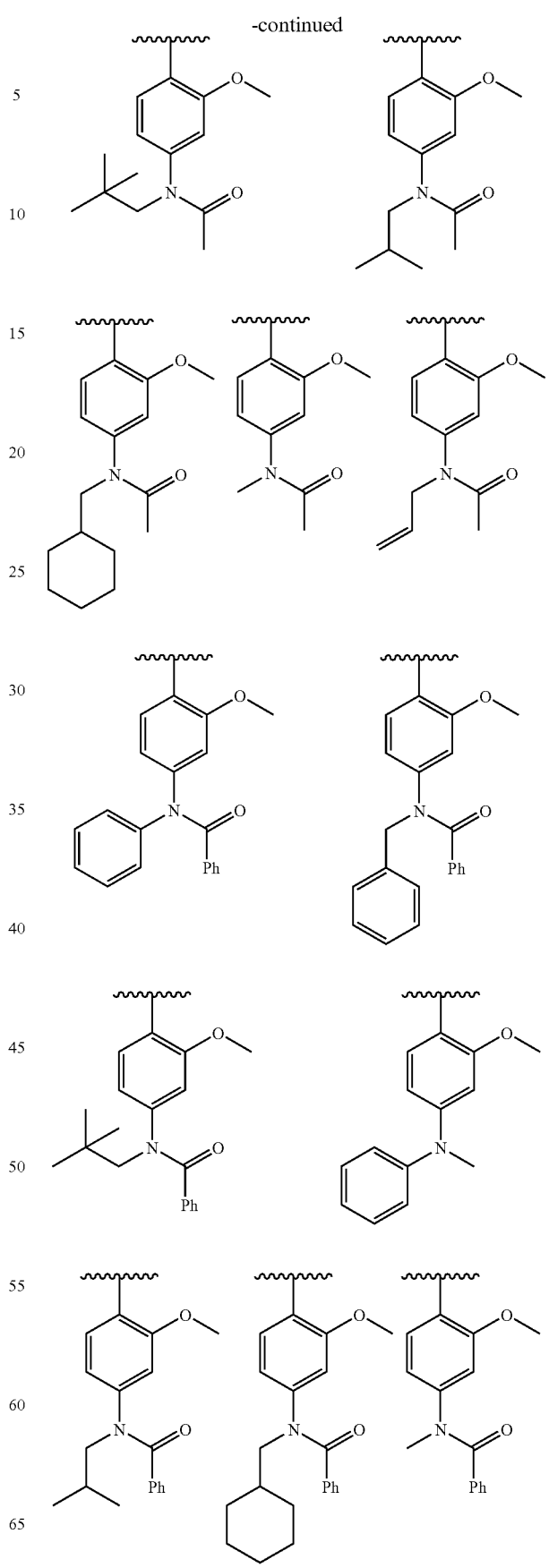

-continued
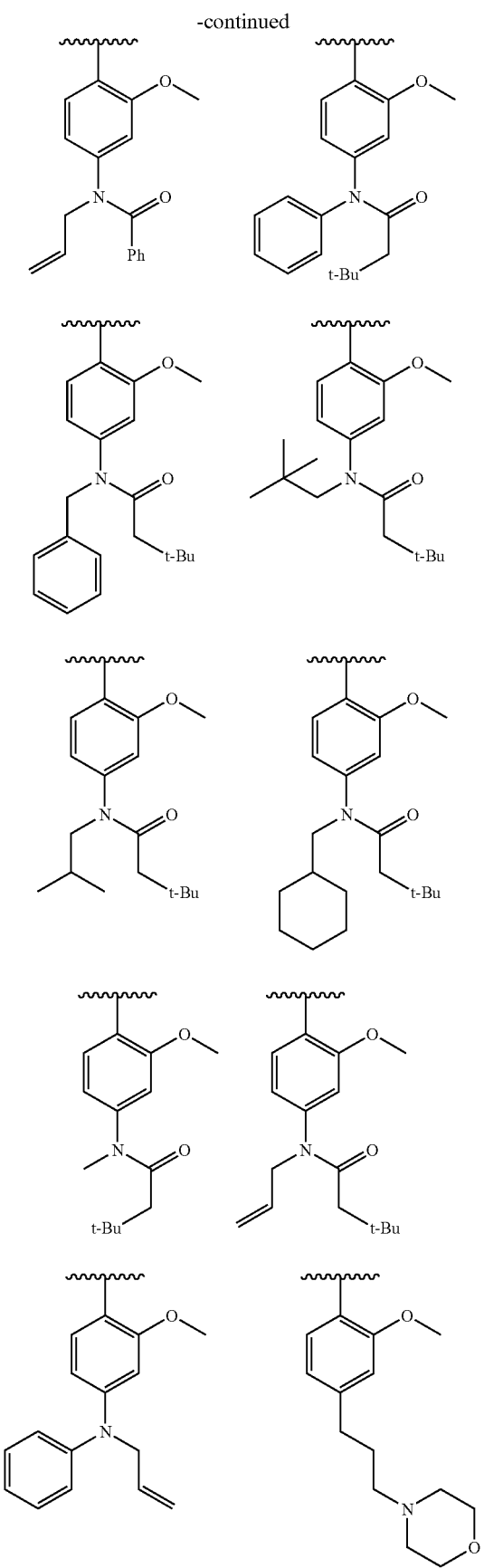
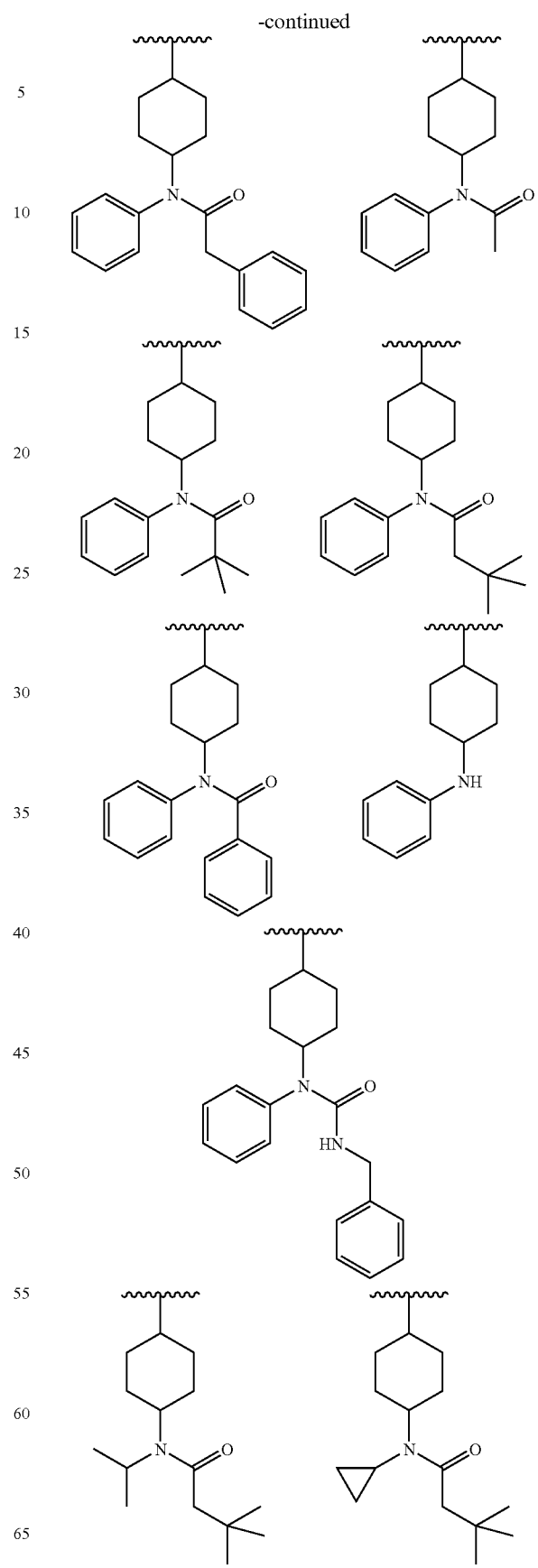

-continued
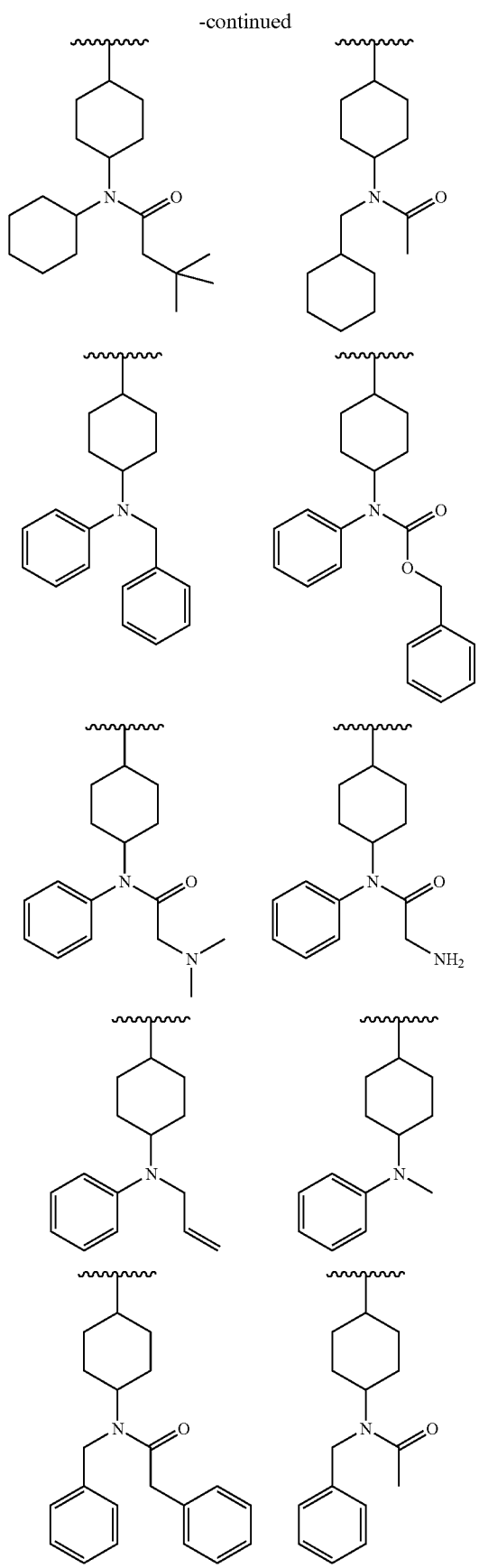
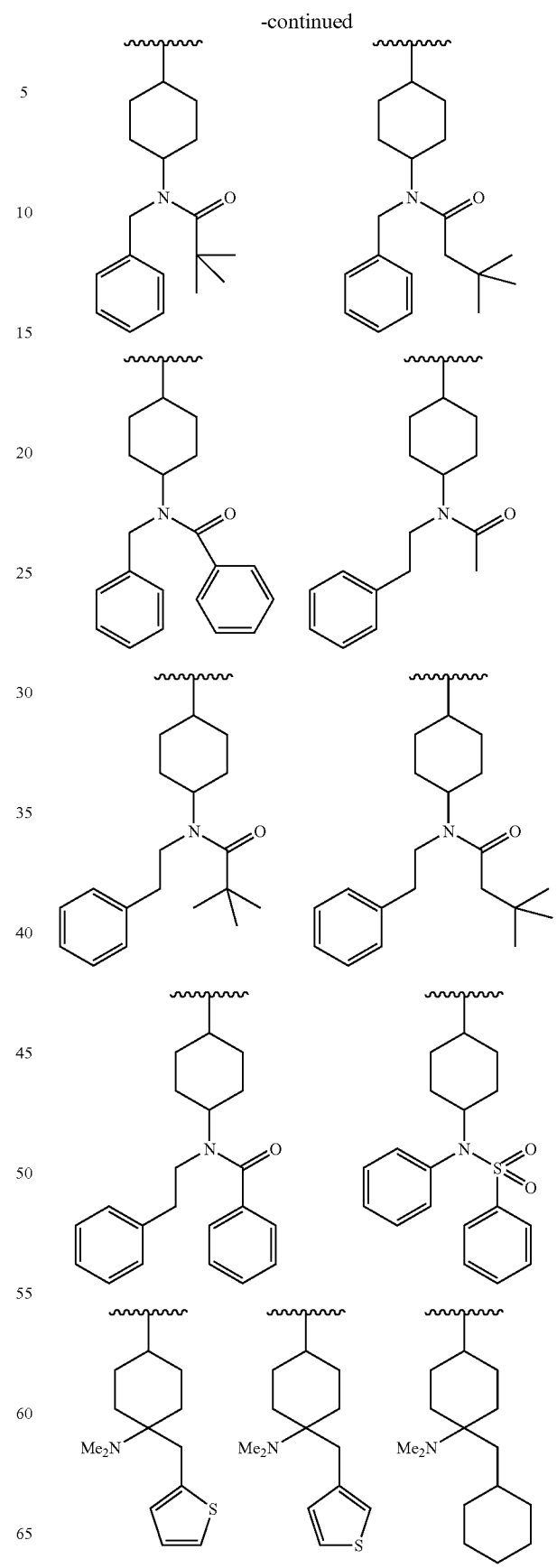

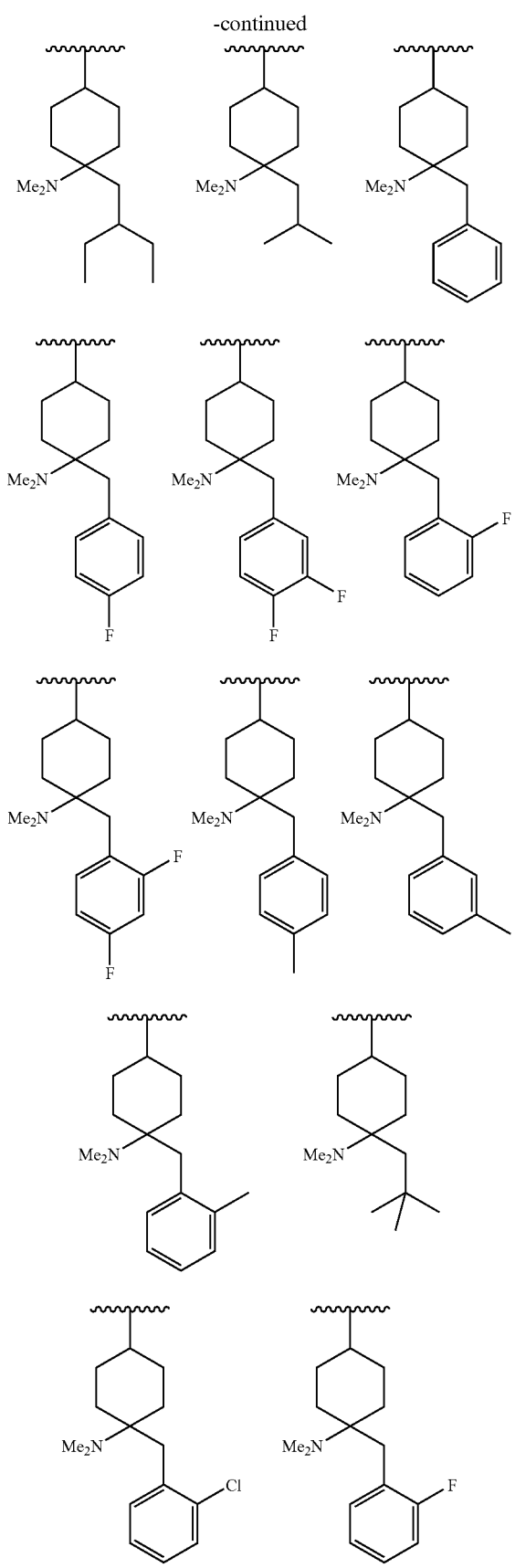
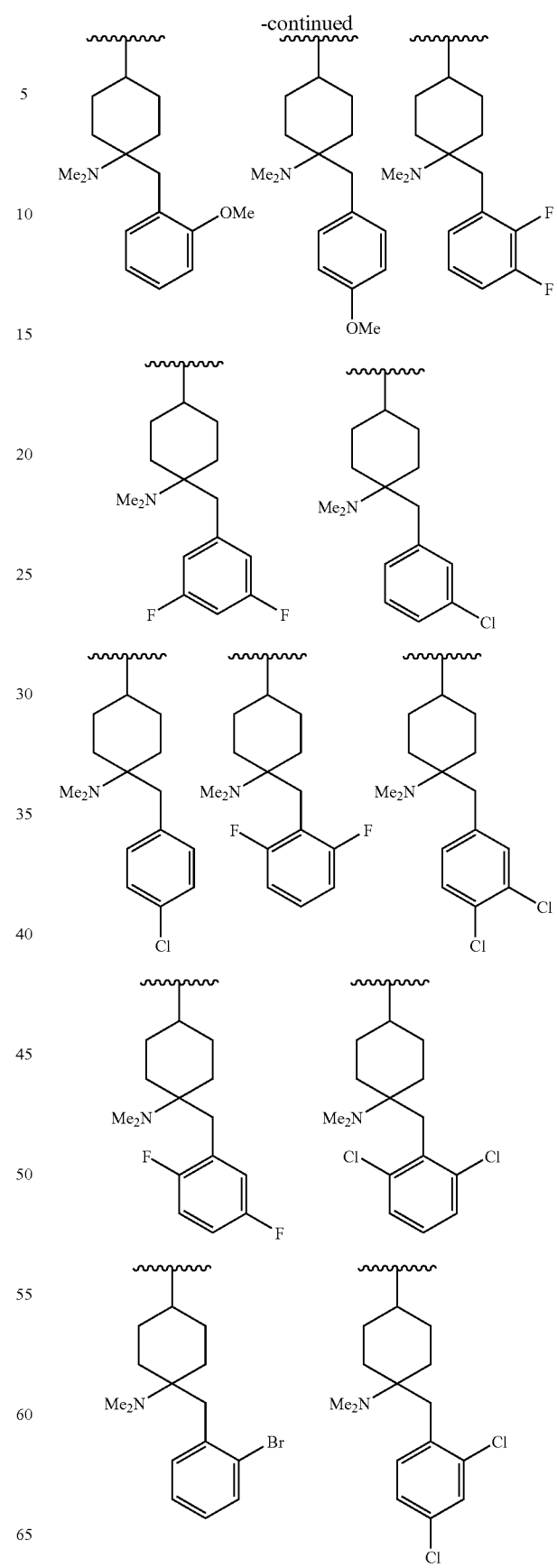

-continued
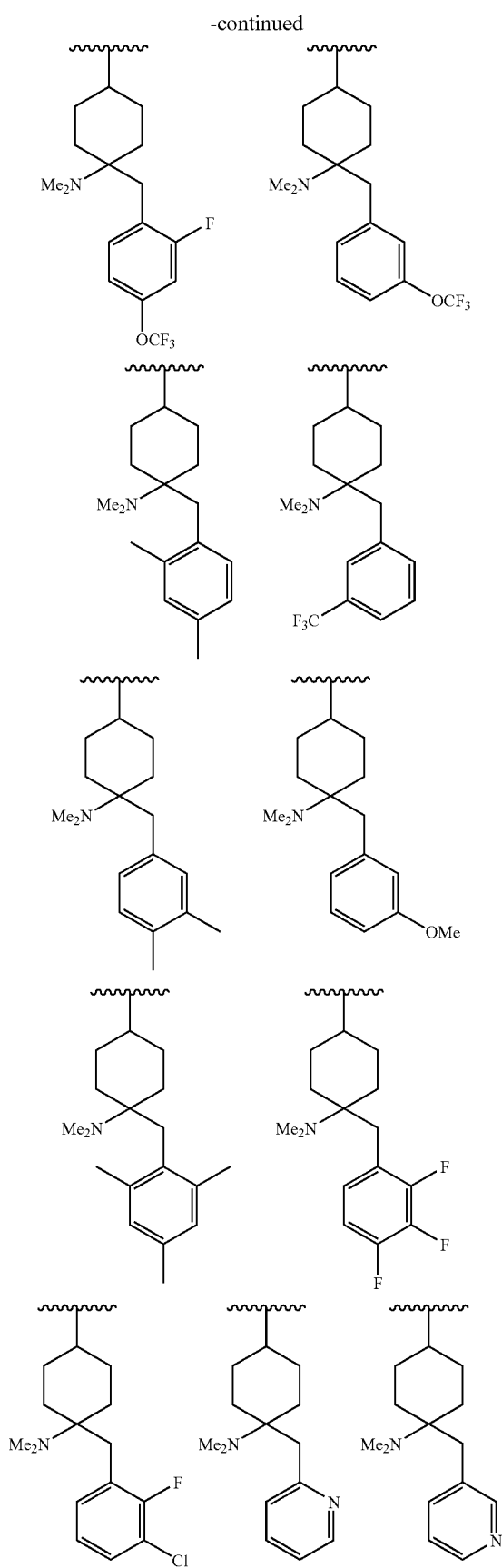
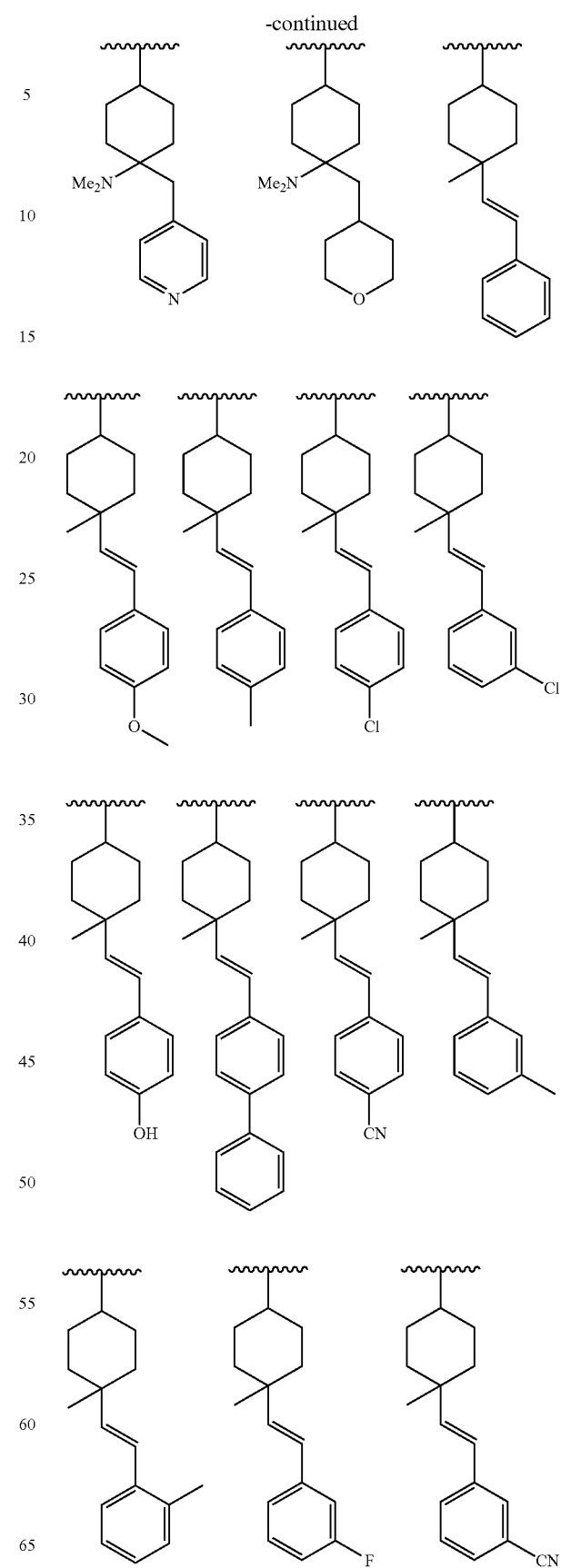

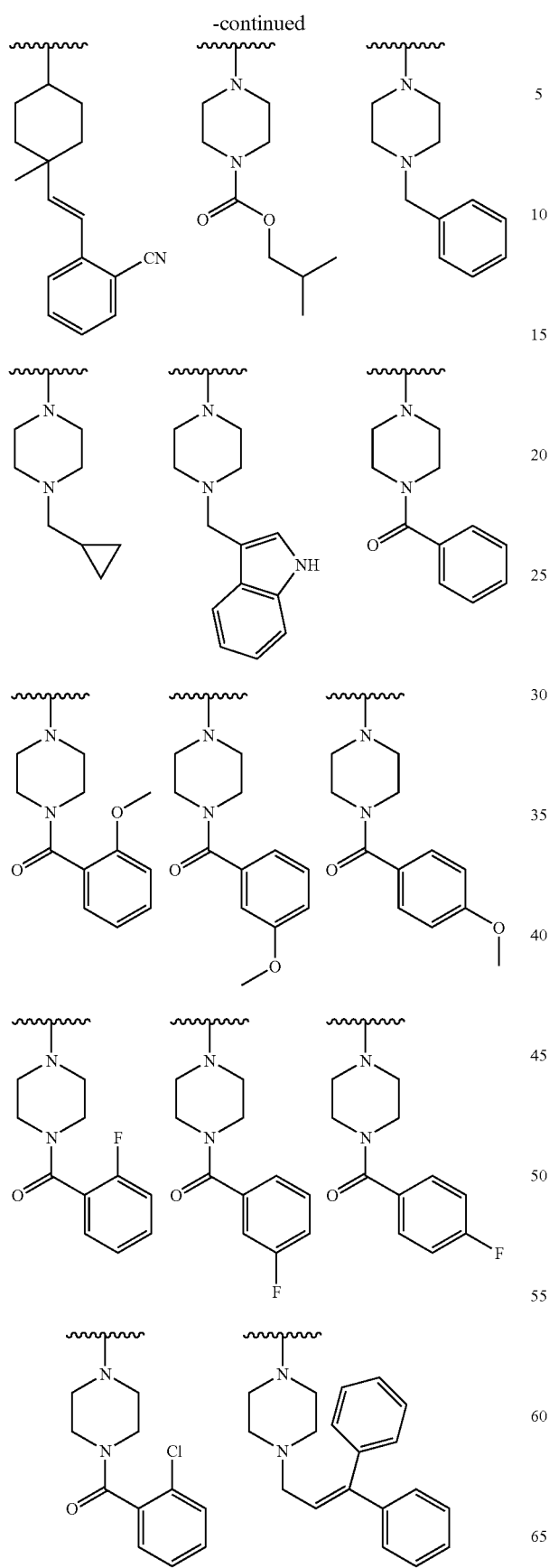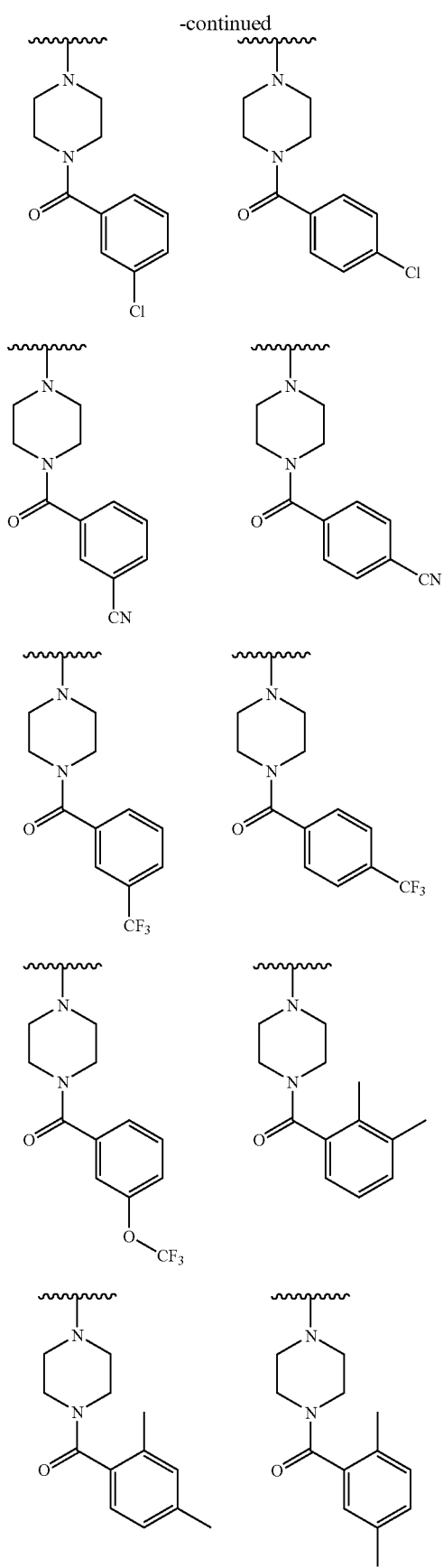

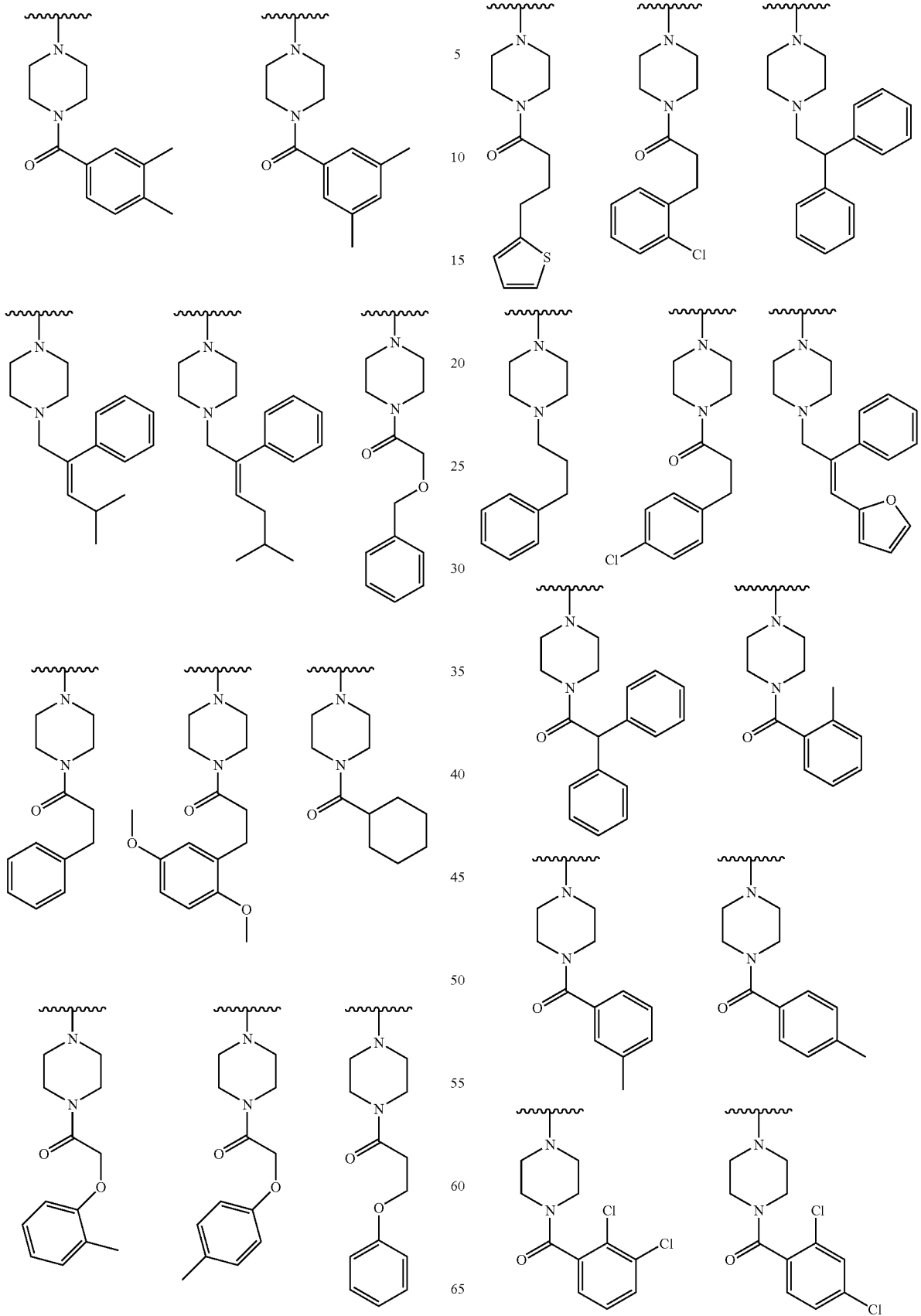

-continued
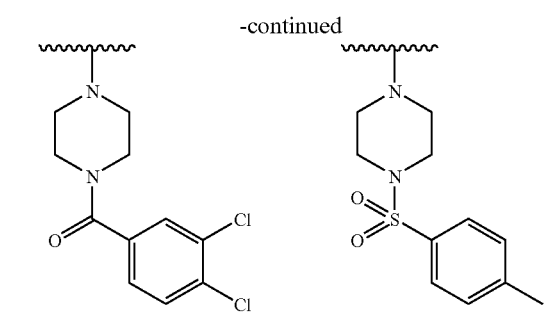
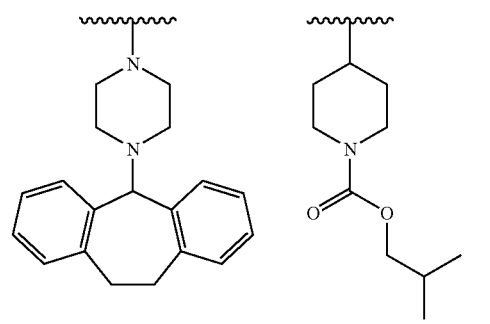
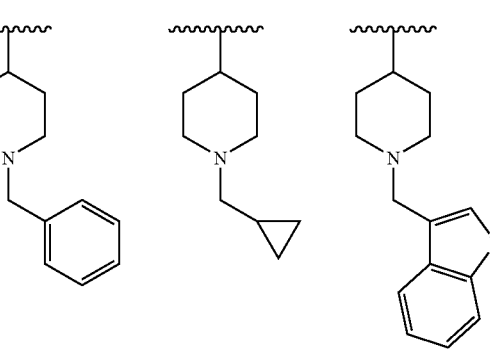
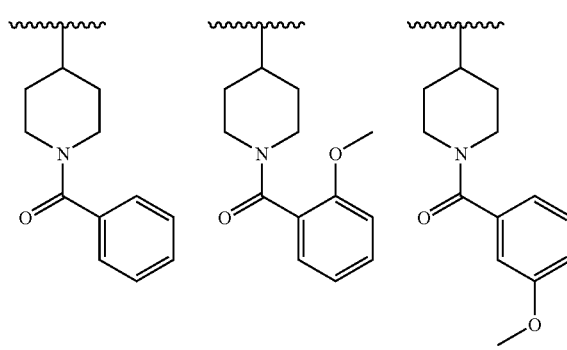
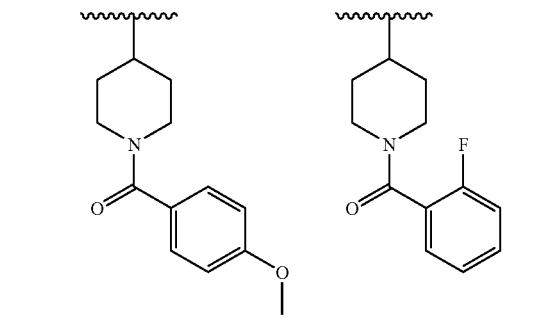
-continued
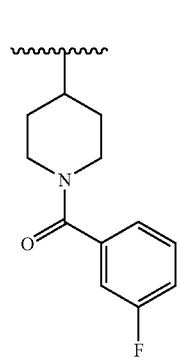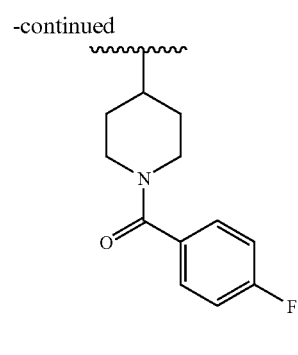
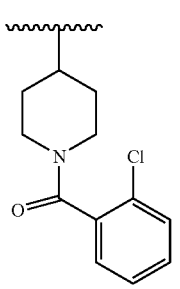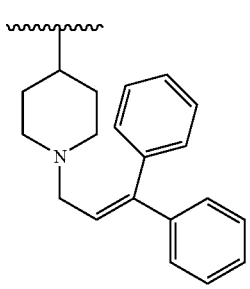
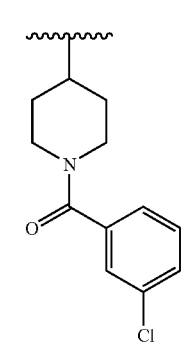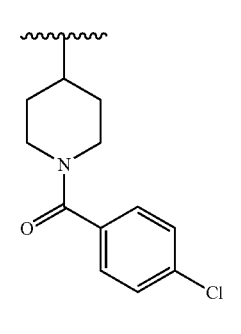
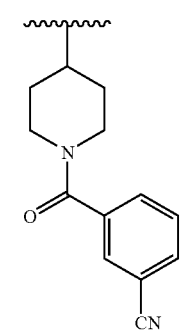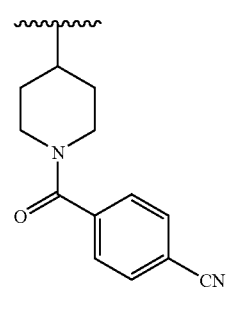
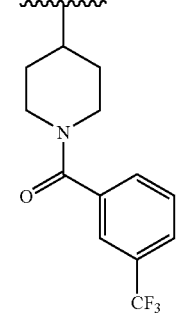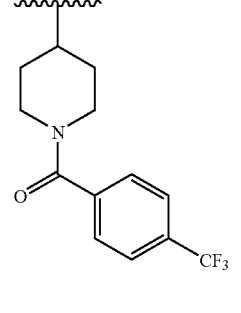

-continued
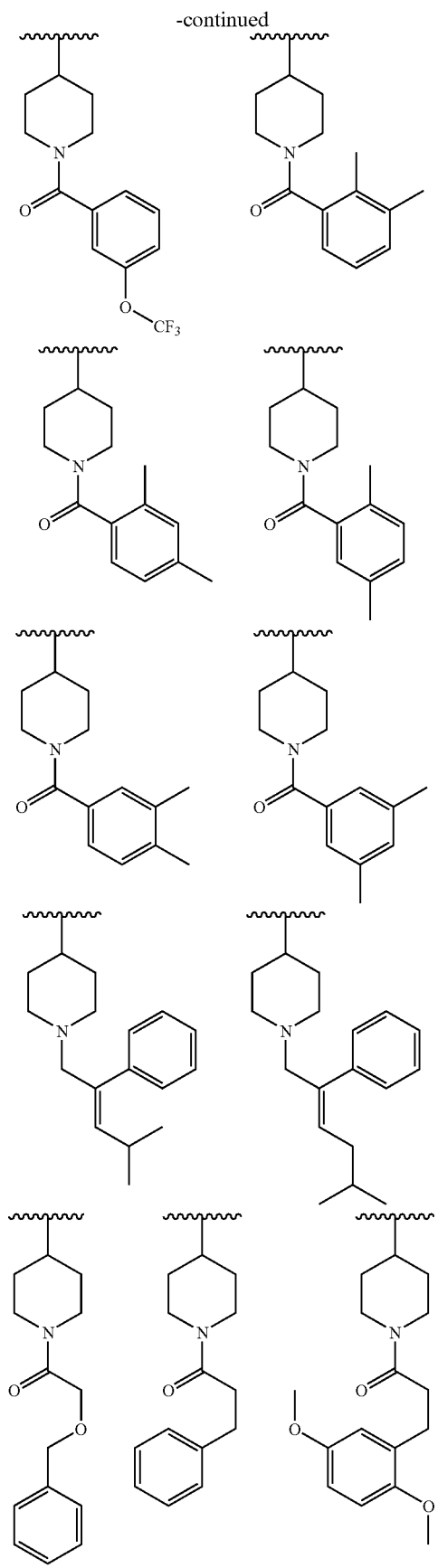
-continued
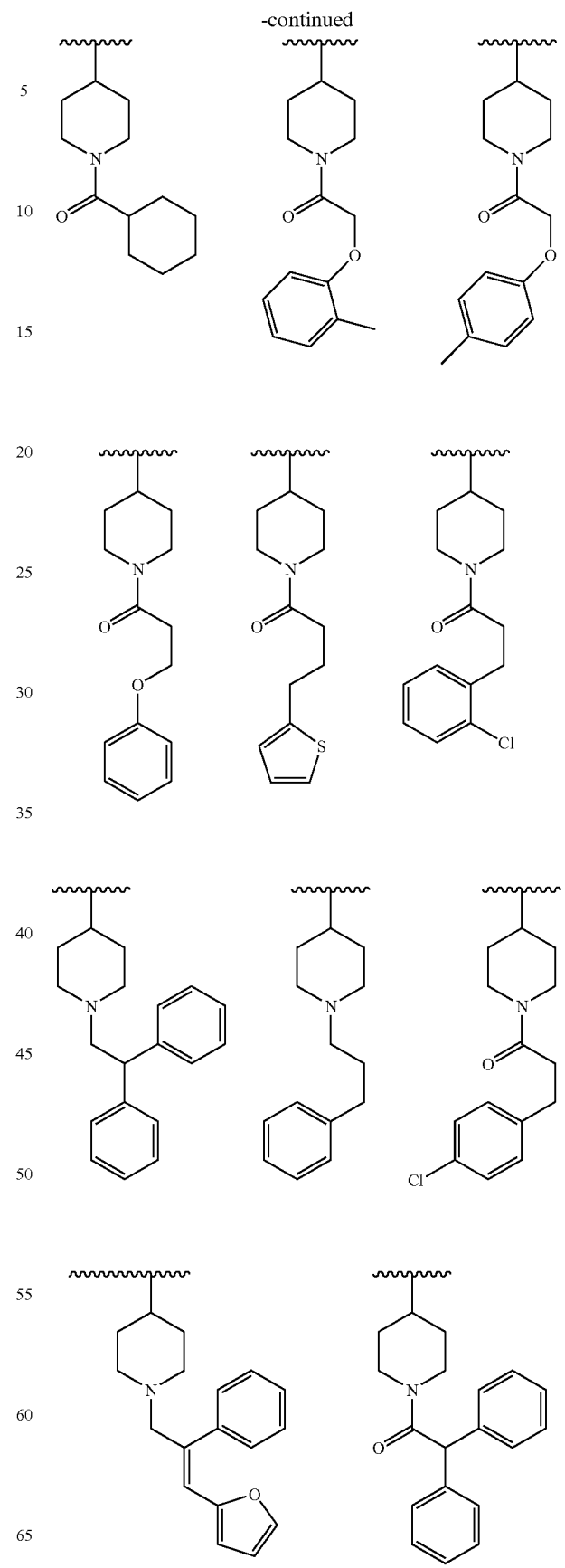

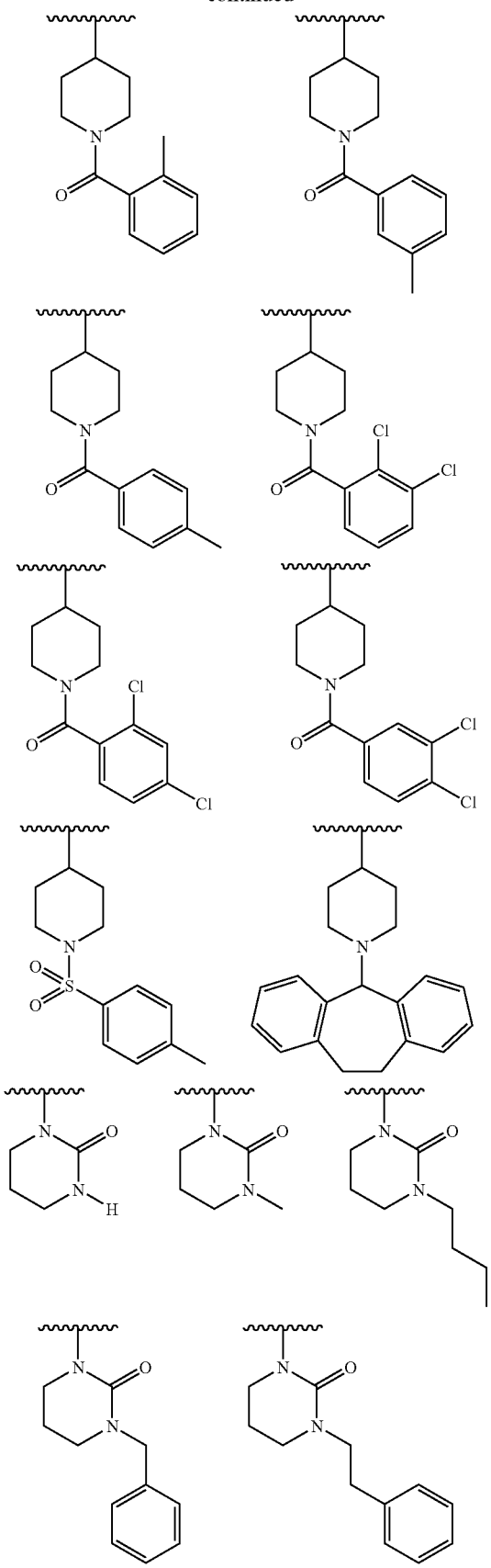
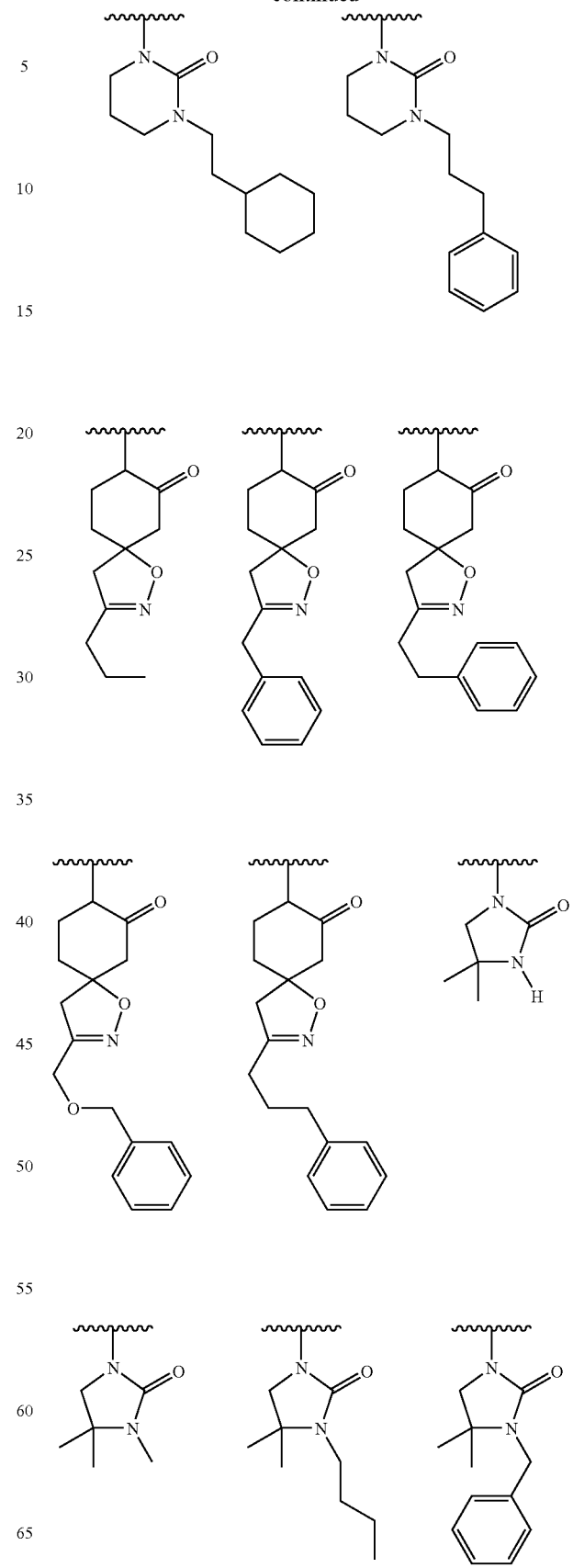

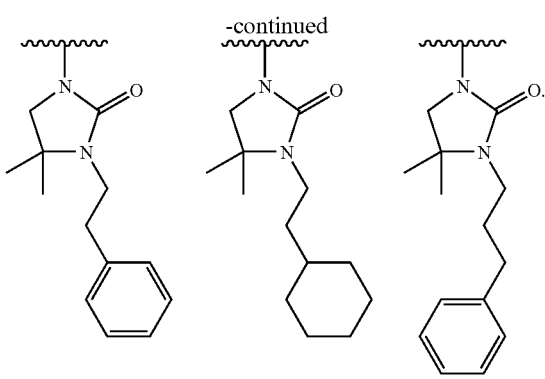

It will be evident to one skilled in the art that the present invention is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound of formula (I)

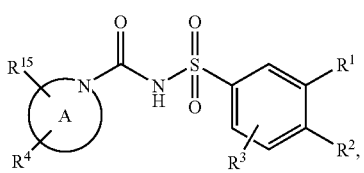

or a therapeutically acceptable salt thereof, wherein
A is piperazine;
$R^1$ is nitro;
$R^2$ is —$NR^5R^6$;
$R^3$ is hydrogen;
$R^4$ is selected from the group consisting of aryl and cycloalkyl wherein the aryl group may be optionally substituted with up to 5 substituents selected from the group consisting of alkyl, nitro, halo, phenylalkoxy, morpholinocarbonylalkyl and morpholinoalkyl and the cycloalkyl group may be optionally substituted with up to 5 substituents selected from the group consisting of alkyl, alkoxy and phenylalkyl;
$R^5$ is hydrogen and $R^6$ is selected from the group consisting of, arylsulfanylalkyl, arylsulfinylalkyl and arylsulfonylalkyl, the alkyl part of each of which is substituted with —$NR^9R^{10}$, wherein $R^9$ and $R^{10}$ are alkyl; and
$R^{15}$ is selected from the group consisting of hydrogen, alkoxy, alkyl, and halo.

2. The compound of claim 1 wherein $R^4$ is cycloalkyl.

3. The compound of claim 2 selected from the group consisting of
N-{[4-({(1R)-5-(dimethylamino)-1-[(phenylthio)methyl]pentyl}amino)-3-nitrophenyl]sulfonyl}-4-(4,4-dimethylcyclohexyl)piperazine-1-carboxamide;
N-{[4-({(1R)-3-(dimethylamino)-1-[(phenylthio)methyl]propyl}amino)-3-nitrophenyl]sulfonyl}-4-(4,4-dimethylcyclohexyl)piperazine-1-carboxamide; and
4-(4-benzyl-4-methoxycyclohexyl)-N-{[4-({(1R)-3-(dimethylamino)-1-[(phenylthio)methyl]propyl}amino)-3-nitrophenyl]sulfonyl}piperazine-1-carboxamide.

4. The compound of claim 1 wherein $R^4$ is aryl.

5. The compound of claim 4 selected from the group consisting of
N-{[4-({(1R)-3-(dimethylamino)-1-[(phenylthio)methyl]propyl}amino)-3-nitrophenyl]sulfonyl}-4-phenylpiperazine-1-carboxamide;
N-{[4-({(1R)-3-(dimethylamino)-1-[(phenylthio)methyl]propyl}amino)-3-nitrophenyl[sulfonyl}-4-(4-nitrophenyl)piperazine-1-carboxamide;
4-[4-(benzyloxy)phenyl]-N-{[4-({(1R)-3-(dimethylamino)-1-[(phenylthio)methyl]propyl}amino)-3-nitrophenyl]sulfonyl}piperazine-1-carboxamide;
N-{[4-({(1R)-3-(dimethylamino)-1-[(phenylthio)methyl]propyl}amino)-3-nitrophenyl]sulfonyl}-4-[4-(3-morpholin-4-yl-3-oxopropyl)phenyl]piperazine-1-carboxamide; and
N-{[4-({(1R)-3-(dimethylamino)-1-[(phenylthio)methyl]propyl}amino)-3-nitrophenyl]sulfonyl}-4-[4-(3-morpholin-4-ylpropyl)phenyl]piperazine-1-carboxamide.

6. A pharmaceutical composition comprising a compound of claim 1 or a therapeutically acceptable salt thereof, in combination with a therapeutically acceptable carrier.

* * * * *